(12) United States Patent
Schottek et al.

(10) Patent No.: US 6,872,843 B2
(45) Date of Patent: Mar. 29, 2005

(54) NON-METALLOCENE COMPOUNDS, METHOD FOR THE PRODUCTION THEREOF AND USE OF THE SAME FOR THE POLYMERIZATION OF OLEFINS

(75) Inventors: Jörg Schottek, Frankfurt (DE); Jörg Schulte, Frankfurt (DE)

(73) Assignee: Basell Polyolefine GmbH (DE)

( * ) Notice: Subject to any disclaimer, the term of this patent is extended or adjusted under 35 U.S.C. 154(b) by 74 days.

(21) Appl. No.: 10/416,948

(22) PCT Filed: Oct. 17, 2001

(86) PCT No.: PCT/EP01/11999

§ 371 (c)(1),
(2), (4) Date: May 15, 2003

(87) PCT Pub. No.: WO02/32908

PCT Pub. Date: Apr. 25, 2002

(65) Prior Publication Data

US 2004/0023940 A1 Feb. 5, 2004

(30) Foreign Application Priority Data

Nov. 17, 2000 (DE) .......................... 100 57 009

(51) Int. Cl.$^7$ .......................... C07F 17/00; B01J 31/00; C08F 4/44

(52) U.S. Cl. .......................... 556/11; 556/12; 556/21; 556/28; 556/43; 556/47; 556/53; 556/58; 556/140; 556/465; 556/482; 502/103; 502/117; 526/351; 526/943

(58) Field of Search .......................... 556/11, 12, 21, 556/28, 43, 47, 53, 58, 140, 465, 482; 502/103, 117; 526/351, 943

(56) References Cited

U.S. PATENT DOCUMENTS

| | | | |
|---|---|---|---|
| 6,124,231 A | 9/2000 | Fritze et al. ............... | 502/152 |
| 6,255,531 B1 | 7/2001 | Fritz et al. ............... | 568/3 |
| 6,329,313 B1 | 12/2001 | Fritze et al. ............... | 502/202 |
| 6,350,829 B1 | 2/2002 | Lynch et al. ............... | 526/151 |

FOREIGN PATENT DOCUMENTS

| | | |
|---|---|---|
| DE | 19606167 | 8/1997 |
| DE | 19622207 | 12/1997 |
| EP | 0302424 | 2/1989 |
| EP | 0601830 | 6/1994 |
| EP | 0811627 | 12/1997 |
| EP | 0824112 | 2/1998 |
| EP | 0824113 | 2/1998 |
| EP | 0874005 | 10/1998 |
| EP | 0924233 | 6/1999 |
| WO | WO 94/28034 | 12/1994 |
| WO | WO 97/11775 | 4/1997 |

OTHER PUBLICATIONS

R. Layer, "The Chemistry of Imines", *B.F. Goodrich Co., Chem Rev*, Dec. 7, 1962.

S. Pasynkiewicz, "Alumoxanes: Synthesis, Structures, Complexes And Reactions", *Polyhedron* 9:2/3, pp. 429–453 (1990).

Harlan et al., "*tert*–Butylaluminum Hydroxides and Oxides: Structural Relationship between Alkylalumoxanes and Alumina Gels", *Organometallics* 13, pp. 2957–2969 (1994).

Chen et al., "Heptane–Soluble Homogeneous Zirconocene Catalyst: Synthesis of a Single Diastereomer, Polymerization Catalysis, and Effect of Silica Supports", *Journal of Polymer Science: Part A: Polymer Chemistry* 33, pp. 2093–2108 (1995).

Harlan et al., "Three–Coordinate Aluminum Is Not a Prerequisite for Catalytic Activity in the Zirconocene—Alumoxane Polymerization of Ethylene", *J. Am. Chem. Soc.* 117, pp. 6465–6474 (1995).

*Primary Examiner*—Porfirio Nazario-Gonzalez
(74) *Attorney, Agent, or Firm*—Connolly Bove Lodge & Hultz LLP

(57) ABSTRACT

The invention relates to a method for producing special transition metal compounds, to novel transition metal compounds and to the use of the same for the polymerisation of olefins.

20 Claims, No Drawings

NON-METALLOCENE COMPOUNDS, METHOD FOR THE PRODUCTION THEREOF AND USE OF THE SAME FOR THE POLYMERIZATION OF OLEFINS

RELATED APPLICATIONS

This application is a 35 U.S.C. § 371 application of PCT/EP01/11999 filed Oct. 17, 2001 which claims benefit to German application 100 57 009.7. filed Oct. 17, 2000.

The present invention relates to a process for preparing specific transition metal compounds, to novel transition metal compounds and to their use for the polymerization of olefins.

In recent years, the polymerization of olefins has been carried out using not only conventional Ziegler catalysts but also metallocenes in order to generate polyolefins having particular properties which are not able to be achieved using conventional Ziegler catalysts. Metallocenes can, if appropriate in combination with one or more cocatalyts, be used as catalyst component for the polymerization and copolymerization of olefins. In particular, halogen-containing metallocenes are used as catalyst precursors which can be converted, for example, by means of an aluminoxane into a polymerization-active cationic metallocene complex.

However, the preparation and use of metallocenes is still a cost factor which has been able to be overcome neither by increased activity nor by improved synthetic methods. In addition, making such catalysts heterogeneous represents a further problem, since, in particular, the activities are greatly decreased, compared to the polymerization carried out homogeneously.

The literature describes various "non-metallocenes", e.g. in EP 874 005, which have advantages in terms of their ease of preparation and the costs of the starting materials. The high activities of these complexes represent a further cost-saving factor.

However, despite numerous compounds known from the literature, "non-metallocenes" which generate isotactic PP having a satisfactory tacticity have not yet been able to be developed to date.

It is an object of the present invention to develop new metal catalysts which provide a new advantageous route to polyolefins and which avoid the disadvantages of the prior art described.

We have found that this object is achieved by a novel ligand structure which is built up from substituted or unsubstituted salicylaldimenes and various silylated indenes and can then be reacted with metal chlorides to give novel metal complexes. This method of preparation provides a universal route to this novel class of compounds. These compounds thus achieve the object of the invention.

The present invention provides compounds of the formula (I):

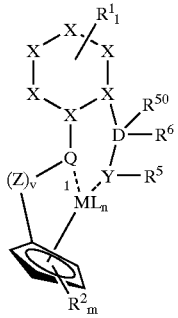

(I)

where
$M^1$ is a metal of transition group III, IV, V or VI of the Periodic Table of the Elements, in particular Ti, Zr, Hf, Ni, Co, Fe, Pd, Sc, Cr and Nb $R^1$ are identical or different and are each a hydrogen atom or $Si(R^{12})_3$, where $R^{12}$ are identical or different and are each a hydrogen atom or a $C_1$–$C_{40}$ group such as $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_6$–$C_{40}$-arylalkenyl, or $R^1$ are identical or different and are each a $C_1$–$C_{30}$ group such as $C_1$–$C_{25}$-alkyl, e.g. methyl, ethyl, tert-butyl, n-hexyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^1$ may be joined to one another so that the radicals $R^1$ and the atoms of the cyclopentadienyl ring which connects them form a $C_4$–$C_{24}$ ring system which may in turn be substituted, $R^2$ are identical or different and are each a hydrogen atom or $Si(R^{12})_3$, where $R^{12}$ are identical or different and are each a hydrogen atom or a $C_1$–$C_{40}$ group such as $C_1$–$C_{20}$-alkyl, $C_1$–$C_{10}$-fluoroalkyl, $C_1$–$C_{10}$-alkoxy, $C_6$–$C_{14}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^2$ are identical or different and are each a $C_1$–$C_{30}$ group such as $C_1$–$C_{25}$-alkyl, e.g. methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl which together with the cyclopentadienyl ring form azapentalenes, thiapentalenes or phosphapentalenes, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicalsmay be joined to one another so that the radicals $R^2$ and the atoms of the cyclopentadienyl ring which connect them form a $C_4$–$C_{24}$ ring system which may in turn be substituted, $R^5$, $R^6$ are identical or different and are each a hydrogen atom or $Si(R^{12})_3$, where $R^{12}$ are identical or different and are each a hydrogen atom or a $C_1$–$C_{40}$ group such as $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^5$ and $R^6$ are identical or different and are each a $C_1$–$C_{30}$ group such as $C_1$–$C_{25}$-alkyl, e.g. methyl, ethyl, tert-butyl, n-hexyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkyaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or the radicals $R^5$ and $R^6$ may be joined to one another so that the radicals $R^5$ and $R^6$ form a $C_2$–$C_{24}$ ring system which may in turn be substituted, $R^{60}$ is a hydrogen atom or a $C_1$–$C_{12}$-alkyl group, preferably a hydrogen atom, l is 5 when v=0 and l is 4 when v=1, m is 5 when v=0 and m is 4 when v=1, D, Q, Y are each an element of main group III, IV, V or VI of the Periodic Table of the Elements, X may be identical or different and are each an element of main group III, IV, V or VI of the Periodic Table of the Elements and may form cyclic systems such as aromatics or aliphatics with one another, L may be identical or different and are each a hydrogen atom, a $C_1$–$C_{10}$-hydrocarbon group such as $C_1$–$C_{10}$-alkyl or $C_6$–$C_{10}$-aryl, a halogen atom or $OR^9$, $SR^9$, $OSiR_3^9$, $SiR_3^9$, $PR_2^9$ or $NR_2^9$, where $R^9$ is a halogen atom, a $C_1$–$C_{10}$-alkyl group, a halogenated $C_1$–$C_{10}$-alkyl group, a $C_6$–$C_{20}$-aryl group or a halogenated $C_6$–$C_{20}$-aryl group, or L is a toluenesulfonyl, trifluoroacetyl, trifluoroacetoxyl, trifluoromethanesulfonyl, nonafluorobutanesulfonyl or 2,2,2-trifluoroethanesulfonyl group, n is an integer from 1 to 4, preferably 2, Z is a bridging structural element and v is 0 or 1.

Examples of Z are $M^2R^{10}R^{11}$ groups, where $M^2$ is carbon, silicon, germanium, boron or tin and $R^{10}$ and $R^{11}$ are identical or different and are each a $C_1$–$C_{20}$-hydrocarbon-containing group such as $C_1$–$C_{10}$-alkyl, $C_6$–$C_{14}$-aryl or trimethylsilyl. Z is preferably $CH_2$, $CH_2CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2Si$, $(C_6H_5)(CH_3)Si$, $(C_6H_5)_2Ge$, $(CH_3)_3Si$—$Si(CH_3)(C_6H_5)_2Sn$, $(CH_2)_4Si$, $(CH_2Si(CH_3)_2$, o-$C_6H_4$ or 2,2'-$(C_6H_4)_2$ or a 1,2-(1-methylethanediyl), 1,2-(1,1-dimethylethanediyl) or 1,2-(1,2-dimethylethanediyl) bridge. It is also possible for Z together with one or more radicals $R^{10}$ and/or $R^{11}$ to form a monocyclic or polycyclic ring system, where $R^{10}$ and $R^{11}$ are as defined above.

Preference is given to bridged organometallic compounds of the formula (I), in particular ones in which v is 1 and the cyclopentadienyl ring is substituted in such a way that it forms an indenyl ring.

Particular preference is given to bridged organometallic compounds of the formula (II),

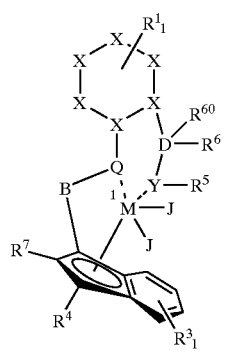

(II)

where $M^1$ is Ti, Zr or Hf, particularly preferably zirconium, $R^1$ are identical or different and are each a hydrogen atom, O—$Si(R^{12})_3$ or $Si(R^{12})_3$, where $R^{12}$ are identical or different and are each a hydrogen atom or a $C_1$–$C_{40}$ group such as $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_{-C40}$-arylalkenyl, or $R^1$ are identical or different and are each a $C_1$–$C_{30}$ group such as $C_1$–$C_{25}$-alkyl, e.g. methyl, ethyl, tert-butyl, n-hexyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^1$ may be joined to one another so that the radicals $R^1$ and the atoms connecting them form a $C_4$–$C_{24}$ ring system which may in turn be substituted, $R^4$, $R^7$ are each a hydrogen atom, a $C_1$–$C_{20}$ group, preferably $C_1$–$C_{18}$-alkyl such as methyl, ethyl, n-butyl, n-hexyl, cyclohexyl or octyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, $R^5$, $R^6$ are identical or different and are each a hydrogen atom or $Si(R^{12})_3$, where $R^{12}$ are identical or different and are each a hydrogen atom or a $C_1$–$C_{40}$ group such as $C_1$–$C_{20}$-alkyl, $C_1$–$C_{10}$-fluoroalkyl, $C_1$–$C_{10}$-alkoxy, $C_8$–$C_{20}$-aryl, $C_8$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^5$ and $R^6$ are identical or different and are each a $C_1$–$C_{30}$ group such as $C_1$–$C_{25}$-alkyl, e.g. methyl, ethyl, tert-butyl, n-hexyl, cyclohexyl or octyl, $C_2$–$C_{25}$-alkenyl, $C_3C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_8$–$C_{24}$-aryl, fluorinated $C_7$–$C_{30}$-arylalkyl, fluorinated $C_7$–$C_{30}$-alkylaryl or $C_1$–$C_{12}$-alkoxy, or the radicals $R^5$ and $R^6$ may be joined to one another so that the radicals $R^5$ and $R^6$ form a $C_4$–$C_{24}$ ring system which may in turn be substituted, $R^3$ is a hydrogen atom, a halogen atom or a $C_1$–$C_{20}$ group, preferably a linear or branched $C_1$–$C_{18}$-alkyl group such as methyl, ethyl, tert-butyl, cyclohexyl or octyl, $C_2$–$C_{10}$-alkenyl, $C_3$–$C_{15}$-alkylalkenyl, a $C_6$–$C_{18}$-aryl group which may be substituted, in particular phenyl, tolyl, xylyl, tert-butylphenyl, ethylphenyl, naphthyl, acenaphthyl, phenanthrenyl or anthracenyl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$arylalkyl or fluorinated $C_7$–$C_{20}$-alkylaryl, or two or more radicals $R^3$ may form a monocyclic or polycyclic ring system which may in turn be substituted, $R^{60}$ is a hydrogen atom or a $C_1$–$C_{12}$-alkyl group, preferably a hydrogen atom, J is a halogen atom, in particular chlorine, an alkyl group such as a $C_1$–$C_{18}$-alkyl group, in particular methyl, ethyl, tert-butyl, or a $C_6$–$C_{15}$-aryl group or a substituted or unsubstituted phenoxide, Q, Y, D are each an element of main group II, IV, V or VI of the Periodic Table of the Elements, in particular boron, carbon, silicon, nitrogen, oxygen or sulfur, X may be identical or different and are each an element of main group III, IV, V or VI of the Periodic Table of the Elements, in particular boron, carbon, silicon, nitrogen, oxygen or sulfur, where the radicals X together form cyclic systems such as aromatics or aliphatics in which one or more carbon atoms may be replaced by N, O, S, B, in particular phenyl, naphthyl, adamantyl, fluorenyl, cyclohexyl, boratabenzene, which may in turn be substituted by $R^1$, l, i are identical or different and are each an integer from 0 to 4, preferably 1 or 2, particularly preferably 1, B is a bridging structural element, $R^{60}$ is a hydrogen atom.

The indenyl ring is preferably substituted by $R^3$, in particular in the 2 position, the 4 position, the 2, 4, 5 positions, the 2, 4, 6 positions, the 2, 4, 7 positions or the 2, 4, 5, 6 positions by $C_1$–$C_{20}$ groups such as $C_1$–$C_{18}$-alkyl or $C_6$–$C_{18}$-aryl, where two or more substituents of the indenyl system may also together form a ring system.

Examples of B are $M^3R^{13}R^{14}$ groups, where $M^3$ is silicon or carbon and $R^{13}$ and $R^{14}$ are each a hydrocarbon-containing group such as $C_1$–$C_{10}$-alkyl, $C_6$–$C_{14}$-aryl or trimethylsilyl. B is preferably $CH_2$, $CH_2CH_2$, $CH(CH_3)CH_2$, $CH(C_4H_9)C(CH_3)_2$, $C(CH_3)_2$, $(CH_3)_2Si$, $(CH^3)_3Si$—$Si(CH_3)$.

Very particular preference is given to bridged organometallic compounds of the formula (II) in which $M^1$ is zirconium, $R^7$ is a hydrogen atom or a linear or branched $C_1$–$C_{12}$-alkyl group, preferably an alkyl group such as methyl, ethyl, n-butyl, n-hexyl, isopropyl, isobutyl, isopentyl, cyclohexyl, cyclopentyl or octyl, particularly preferably methyl, ethyl, isopropyl or cyclohexyl, $R^5$ is a hydrogen atom, a halogen atom or a $C_1$–$C_{20}$ group, preferably a linear or branched $C_1$–$C_8$-alkyl group such as methyl, ethyl, tert-butyl, cyclohexyl or octyl, $C_2$–$C_6$-alkenyl, $C_3$–$C_6$-alkylalkenyl, a $C_6$–$C_{18}$-aryl group which may be substituted, in particular phenyl, tolyl, xylyl, tert-butylphenyl, ethylphenyl, naphthyl, acenaphthyl, penanthrenyl or anthracenyl, $C_5$–$C_{18}$-heteroaryl, $C_7$–$C_{12}$-arylalkyl, $C_7$–$C_{12}$-alkylaryl, fluorinated $C_1$–$C_8$-alkyl, fluorinated $C_6$–$C_{18}$-aryl, fluorinated $C_7$–$C_{12}$-arylalkyl or fluorinated $C_7$–$C_{12}$-alkylaryl, $R^6$ are identical or different and are each a hydrogen atom or a $C_1$–$C_{12}$-alkyl group, preferably an alkyl group such as methyl, ethyl, n-butyl, n-hexyl or octyl, particularly preferably methyl or ethyl, $R^3$ is a hydrogen atom, a halogen atom or a $C_1$–$C_{20}$ group, preferably a linear or branched $C_1$–$C_8$-alkyl group such as methyl, ethyl, tert-butyl, cyclohexyl or octyl, $C_2$–$C_6$-alkenyl, $C_3$–$C_6$-alkylalkenyl, a $C_6$–$C_{18}$-aryl group, in particular phenyl, tolyl, xylyl, tert-butylphenyl, ethylphenyl, naphthyl, acenaphthyl, penanthrenyl or anthracenyl, preferably a $C_6$–$C_{18}$-aryl group which is substituted, $C_5$–$C_{18}$-heteroaryl, $C_7$–$C_{12}$-arylalkyl, $C_7$–$C_{12}$-alkylaryl, fluorinated $C_1$–$C_8$-alkyl, fluorinated $C_6$–$C_{18}$-aryl, fluorinated $C_7$–$C_{12}$-arylalkyl or fluorinated $C_7$–$C_{12}$-alkylaryl, J is chlorine or methyl, Q, Y. D are each, independently of one another, an element of main group IV, V or VI of the Periodic Table of the Elements, in particular carbon, nitrogen, sulfur or oxygen, X may be identical or different and are each an element of main group IV, V or VI of the Periodic Table of the Elements, in particular carbon, nitrogen, oxygen or sulfur, in particular phenyl, naphthyl, cyclohexyl which may in turn be substituted by $R^1$, l, i are identical or different and are each an integer from 0 to 4, preferably 1 or 2, particularly preferably 1, B is a bridging structural element, preferably $Si(Me)_2$, $Si(Ph)_2$, $Si(Et)_2$, $Si(MePh)$, $CH_2$, $CH_2CH_2$, $(CH_3)_2Si$—$Si(CH_3)$.

In the above radicals, Ph is substituted or unsubstituted phenyl, Et is ethyl and Me is methyl.

The invention further provides ligand systems of the formula (IIa), in which the radicals are as defined under formula (II).

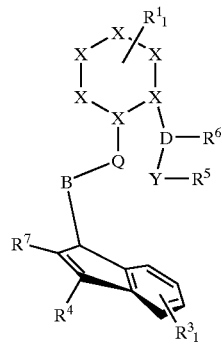

(IIa)

Illustrated but nonlimiting examples of novel compounds of the formula (II) are:

dimethylsilanyloxy(L)(indenyl) zirconium dichloride dimethylsilanyloxy(L)(4-naphthylindenyl)zirconium dichloride dimethylsilanyloxy(L)(2-methylbenzoindenyl)zirconium dichloride dimethylsilanyloxy(L)(2-methylindenyl)zirconium dichloride dimethylsilanyloxy(L)(2-methyl-4-(1-naphthyl)indenyl) zirconium dichloride dimethylsilanyloxy(L)(2-methyl-4-(2-naphthyl)indenyl) zirconium dichloride dimethylsilanyloxy(L)(2,7-methyl-4-(1-naphthyl)indenyl) zirconium dichloride dimethylsilanyloxy(L)(2,7-methyl-4-(2-naphthyl)indenyl) zirconium dichloride dimethylsilanyloxy(L)(2-methyl-4-phenylindenyl) zirconium dichloride dimethylsilanyloxy(L)(2,7-methyl-4-phenylindenyl) zirconium dichloride dimethylsilanyloxy(L)(2-methyl-4-(4'-tert-butylphenyl-indenyl)zirconium dichloride dimethylsilanyloxy(L)(2-methyl-4-t-butylindenyl) zirconium dichloride dimethylsilanyloxy(L)(2-methyl-4-isopropylindenyl) zirconium dichloride dimethylsilanyloxy(L)(2-methyl-4-ethylindenyl)zirconium dichloride dimethylsilanyloxy(L)(2-methyl-4-acenaphthindenyl) zirconium dichloride dimethylsilanyloxy(L)(2,4-dimethylindenyl)zirconium dichloride dimethylsilanyloxy(L)(2-ethylindenyl)zirconium dichloride dimethylsilanyloxy(L)(2-ethyl-4-ethylindenyl)zirconium dichloride dimethylsilanyloxy(L)(2-ethyl-4-phenylindenyl)zirconium dichloride dimethylsilanyloxy(L)(2-methyl-4,5-benzoindenyl) zirconium dichloride dimethylsilanyloxy(L)(2-methyl-4,6-diisopropylindenyl) zirconium dichloride dimethylsilanyloxy(L)(2-methyl-4,5-diisopropylindenyl) zirconium dichloride dimethylsilanyloxy(L)(2,4,6-trimethylindenyl)zirconium dichloride dimethylsilanyloxy(L)(2,5,6-trimethylindenyl)zirconium dichloride dimethylsilanyloxy(L)(2,4,7-trimethylindenyl)zirconium dichloride dimethylsilanyloxy(L)(2-methyl-5-isobutylindenyl) zirconium dichloride dimethylsilanyloxy(L)(2-methyl-5-t-butylindenyl) zirconium dichloride
methyl(phenyl)silanyloxy(L)(2-methyl-4-phenylindenyl) zirconium dichloride
methyl(phenyl)silanyloxy(L)(2-methyl-4,6-diisopropyl-indenyl)zirconium dichloride
methyl(phenyl)silanyloxy(L)(2-methyl-4-isopropylindenyl) zirconium dichloride
methyl(phenyl)silanyloxy(L)(2-methyl-4,5-benzoindenyl) zirconium dichloride
methyl(phenyl)silanyloxy(L)(2-methyl-4,5-(methylbenzo) indenyl)zirconium dichloride
methyl(phenyl)silanyloxy(L)(2-methyl-4-acenaphthin-denyl)zirconium dichloride
methyl(phenyl)silanyloxy(L)(2-methyl-4-acenaphthin-denyl)zirconium dichloride
methyl(phenyl)silanyloxy(L)(2-methylindenyl) zirconium dichloride
methyl(phenyl)silanyloxy(L)(2-methyl-5-isobutylindenyl) zirconium dichloride
1,2-ethanediyloxy(L)(2-methyl-4-phenylindenyl)zirconium dichloride
1,4-butanediyloxy(L)(2-methyl-4-phenylindenyl)zirconium dichloride
1,2-ethanediyloxy(L)(2-methyl-4,6-diisopropylindenyl) zirconium dichloride
1,4-butanediyloxy(L)(2-methyl-4-isopropylindenyl) zirconium dichloride
1,4-butanediyloxy(L)(2-methyl-4,5-benzoindenyl) zirconium dichloride
1,2-ethanediyloxy(L)(2-methyl-4,5-benzoindenyl) zirconium dichloride
1,2-ethanediyloxy(L)(2,4,7-trimethylindenyl)zirconium dichloride
1,2-ethanediyloxy(L)(2-methylindenyl)zirconium dichloride
1,4-butanediyloxy(L)(2-methylindenyl)zirconium dichoride
(L)-(cyclopentadienyl)zirconium dichloride
(L)-(n-butylcyclopentadienyl)zirconium dichloride
(L)-(1,3-dimethylcyclopentadienyl)zirconium dichloride
tetrachloro[1[(L)($\eta^5$-1H-inden-1-ylidene)methylsilyl]-3-$\eta^5$-cyclopenta-2,4-dien-1-ylidene)-3-$\eta^5$-9H-fluoren-9-ylidene)butane]dizirconium
tetrachloro[2[(L)($\eta^5$-2-methyl-1H-inden-1-ylidene) methoxysilyl]-5-($\eta^5$-2,3,4,5-tetramethylcyclopenta-2,4-dien-1-ylidene)-5-($\eta^5$-9H-fluoren-9-ylidene)hexane] dizirconium
tetrachloro[1[(L)($\eta^5$-1H-inden-1-ylidene)methylsilyl]-6-($\eta^5$-cyclopenta-2,4-dien-1-ylidene)-6-($\eta^5$-9H-fluoren-9-ylidene)-3-oxaheptane]dizirconium
dimethylsilanyloxy(L)(2-methyl-4-(tert-butylphenylin-denyl)zirconium dichloride
dimethylsilanyloxy(L)(2-methyl-4-(4-methylphenylin-denyl)zirconium dichloride
dimethylsilanyloxy(L)(2-methyl-4-(4-ethylphenylindenyl) zirconium dichloride
dimethylsilanyloxy(L)(2-methyl-4-(4-trifluoromethyl-phenylindenyl)zirconium dichloride
dimethylsilanyloxy(L)(2-methyl-4-(4-methoxyphenylin-denyl)zirconium dichloride
dimethylsilanyloxy(L)(2-ethyl-4-(4-tert-butylphenyl-indenyl)zirconium dichloride
dimethylsilanyloxy(L)(2-ethyl-4-(4-methylphenylindenyl) zirconium dichloride
dimethylsilanyloxy(L)(2-ethyl-4-(4-ethylphenylindenyl) zirconium dichloride
dimethylsilanyloxy(L)(2-ethyl-4-(4-trifluoromethylphenyl-indenyl)zirconium dichloride
dimethylsilanyloxy(L)(2-ethyl-4-(4-methoxyphenyl-indenyl)zirconium dichloride
dimethylsilanyloxy(L)(2-methyl-4-(4-tert-butylphenyl-indenyl)dimethylzirconium
dimethylsilanyloxy(L)(2-methyl-4-(4-methylphenyl-indenyl)dimethylzirconium
dimethylsilanyloxy(L)(2-methyl-4-(4-ethylphenylindenyl) dimethylzirconium
dimethylsilanyloxy(L)(2-methyl-4-(4-trifluoromethyl-phenylindenyl)dimethylzirconium
dimethylsilanyloxy(L)(2-methyl-4-(4-methoxyphenyl-indenyl)dimethylzirconium
dimethylsilanyloxy(L)(2-ethyl-4-(4-tert-butylphenyl-indenyl)dimethylzirconium
dimethylsilanyloxy(L)(2-ethyl-4-(4-methylphenylindenyl) dimethylzirconium
dimethylsilanyloxy(L)(2-ethyl-4-(4-ethylphenylindenyl) dimethylzirconium
dimethylsilanyloxy(L)(2-ethyl-4-(4-trifluoromethylphenyl-indenyl)dimethylzirconium
dimethylsilanyloxy(L)(2-ethyl-4-(4-methoxyphenyl-indenyl)dimethylzirconium
dimethylsilanyloxy(L)(2-methyl-4-(4'-tert-butylphenyl) indenyl)zirconium dichloride
dimethylsilanyloxy(L)(2-isopropyl-7-methyl-4-(4'-tert-butylphenyl)indenyl)zirconium dichloride
dimethylsilanyloxy(L)(2,7-methyl-4-(4'-tert-butylphenyl) indenyl)zirconium dichloride
dimethylsilanyloxy(L)(2-methyl-4-(4'-tert-butylphenyl) indenyl)hafnium dichloride
dimethylsilanyloxy(L)(2-methyl-4-(4'-tert-butylphenyl) indenyl)titanium dichloride
dimethylsilanyloxy(L)(2-ethyl-7-methyl-4-(4'-tert-butylphenyl)indenyl)zirconium dichloride
dimethylsilanyloxy(L)(2-methyl-4-(4'-methylphenyl) indenyl)zirconium dichloride
dimethylsilanyloxy(L)(2-methyl-4-(4'-n-propylphenyl) indenyl)zirconium dichloride
dimethylsilanyloxy(L)(2-methyl-4-(4'-n-butylphenyl) indenyl)zirconium dichloride
dimethylsilanyloxy(L)(2-methyl-4-(4-hexylphenyl)indenyl) zirconium dichloride
dimethylsilanyloxy(L)(2-methyl-4-(4'-sec-butylphenyl) indenyl)zirconium dichloride
dimethylsilanyloxy(L)(2-ethyl-4-phenyl)indenyl)zirconium dichloride
dimethylsilanyloxy(L)(2-ethyl-4-(4'-methylphenyl)indenyl) zirconium dichloride
dimethylsilanyloxy(L)(2-ethyl-4-(4'-ethylphenyl)indenyl) zirconium dichloride
dimethylsilanyloxy(L)(2-ethyl-4-(4'-n-propylphenyl) indenyl)zirconium dichloride
dimethylsilanyloxy(L)(2-ethyl-4-(4'-n-butylphenyl)indenyl) zirconium dichloride
dimethylsilanyloxy(L)(2-ethyl-4-(4'-hexylphenyl)indenyl) zirconium dichloride
dimethylsilanyloxy(L)(2-ethyl-4-(4'-pentylphenyl)indenyl) zirconium dichloride
dimethylsilanyloxy(L)(2-ethyl-4-(4'-cyclohexylphenyl) indenyl)zirconium dichloride
dimethylsilanyloxy(L)(2-ethyl-4-(4'-sec-butylphenyl) indenyl)zirconium dichloride
dimethylsilanyloxy(L)(2-ethyl-4-(4'-tert-butylphenyl) indenyl)zirconium dichloride
dimethylsilanyloxy(L)(2-n-propyl-4-phenyl)indenyl) zirconium dichloride
dimethylsilanyloxy(L)(2-n-propyl-4-(4'-methylphenyl) indenyl)zirconium dichloride dimethylsilanyloxy(L)(2-n-propyl-4-(4'-ethylphenyl)indenyl)zirconium dichloride
dimethylsilanyloxy(L)(2-n-propyl-4-(4'-isopropylphenyl)indenyl)zirconium dichloride
dimethylsilanyloxy(L)(2-n-propyl-4-(4'-n-butylphenyl)indenyl)zirconium dichloride
dimethylsilanyloxy(L)(2-n-propyl-4-(4'-hexylphenyl)indenyl)zirconium dichloride
dimethylsilanyloxy(L)(2-n-propyl-4-(4'-cyclohexylphenyl)indenyl)zirconium dichloride
dimethylsilanyloxy(L)(2-n-propyl-4-(4'-sec-butylphenyl)indenyl)zirconium dichloride
dimethylsilanyloxy(L)(2-n-propyl-4-(4'-tert-butylphenyl)indenyl)zirconium dichloride
dimethylsilanyloxy(L)(2-n-butyl-4-phenyl)indenyl)zirconium dichloride
dimethylsilanyloxy(L)(2-n-butyl-4-(4'-methylphenyl)indenyl)zirconium dichloride
dimethylsilanyloxy(L)(2-n-butyl-4-(4'-ethylphenyl)indenyl)zirconium dichloride
dimethylsilanyloxy(L)(2-n-butyl-4-(4'-n-propylphenyl)indenyl)zirconium dichloride
dimethylsilanyloxy(L)(2-n-butyl-4-(4'-isopropylphenyl)indenyl)zirconium dichloride
dimethylsilanyloxy(L)(2-n-butylphenyl)indenyl)zirconium dichloride
dimethylsilanyloxy(L)(2-n-butyl-4-(4'-hexylphenyl)indenyl)zirconium dichloride
dimethylsilanyloxy(L)(2-n-butyl-4-(4'-cyclohexylphenyl)indenyl)zirconium dichloride
dimethylsilanyloxy(L)(2-n-butyl-4-(4'-sec-butylphenyl)indenyl)zirconium dichloride
dimethylsilanyloxy(L)(2-n-butyl-4-(4'-tert-butylphenyl)indenyl)zirconium dichloride
dimethylsilanyloxy(L)(2-hexyl-4-phenyl)indenyl)zirconium dichloride
dimethylsilanyloxy(L)(2-hexyl-4-(4'-methylphenyl)indenyl)zirconium dichloride
dimethylsilanyloxy(L)(2-hexyl-4-(4'ethylphenyl)indenyl)zirconium dichloride
dimethylsilanyloxy(L)(2-hexyl-4-(4'-n-propylphenyl)indenyl)zirconium dichloride
dimethylsilanyloxy(L)(2-hexyl-4-(4'-isopropylphenyl)indenyl)zirconium dichloride
dimethylsilanyloxy(L)(2-hexyl-4-(4'-n-butylphenyl)indenyl)zirconium dichloride
dimethylsilanyloxy(L)(2-hexyl-4-(4'-hexylphenyl)indenyl)zirconium dichloride
dimethylsilanyloxy(L)(2-hexyl-4-(4'-cyclohexylphenyl)indenyl)zirconium dichloride
dimethylsilanyloxy(L)(2-hexyl-4-(4'-sec-butylphenyl)indenyl)zirconium dichloride
dimethylsilanyloxy(L)(2-hexyl-4-(4'-tert-butylphenyl)indenyl)zirconium dichloride
dimethylsilanyloxy(L)(2-methyl-4-(4'-tert-butylphenyl)indenyl)zirconium(L)(dimethylamide)
dimethylsilanyloxy(L)(2-ethyl-4-(4'-tert-butylphenyl)indenyl)dibenzyl zirconium
dimethylsilanyloxy(L)(2-methyl-4-(4'-tert-butylphenyl)indenyl)dimethyl zirconium
dimethylgermanyloxy(L)(2-ethyl-4-(4'-tert-butylphenyl)indenyl)zirconium dichloride
dimethylgermanyloxy(L)(2-ethyl-4-(4'-tert-butylphenyl)indenyl)hafnium dichloride
dimethylgermanyloxy(L)(2-propyl-4-(4'-tert-butylphenyl)indenyl)titanium dichloride
dimethylgermanyloxy(L)(2-methyl-4-(4'-tert-butylphenyl)indenyl)zirconium dichloride
ethylidenoxy(L)(2-ethyl-4-phenyl)indenyl)zirconium dichloride
ethylidenoxy(L)(2-ethyl-4-(4'-tert-butylphenyl)indenyl)zirconium dichloride
ethylidenoxy(L)(2-n-propyl-4-(4'-tert-butylphenyl)indenyl)zirconium dichloride
ethylidenoxy(L)(2-n-butyl-4-(4'-tert-butylphenyl)indenyl)titanium dichloride
ethylidenoxy(L)(2-hexyl-4-(4'-tert-butylphenyl)indenyl)dibenzyl zirconium
ethylidenoxy(L)(2-ethyl-4-(4'-tert-butylphenyl)indenyl)dibenzylhafnium
ethylidenoxy(L)(2-methyl-4-(4'-tert-butylphenyl)indenyl)dibenzyltitanium
ethylidenoxy(L))2-methyl-4-(4'-tert-butylphenyl)indenyl)zirconium dichloride
ethylidenoxy(L)(2-ethyl-4-(4'-tert-butylphenyl)indenyl)dimethylhafnium
ethylidenoxy(L(2-n-propyl-4-phenyl)indenyl)dimethyltitanium
ethylidenoxy(L)(2-ethyl-4-(4'-tert-butylphenyl)indenyl)zirconium bis(dimethylamide)
ethylidenoxy(L)(2-ethyl-4-(4'-tert-butylphenyl)indenyl)hafnium bis(dimethylamide)
ethylidenoxy(L)(2-ethyl-4-(4'-tert-butylphenyl)indenyl)titanium bis(dimethylamide)
methylethylidenoxy(L)(2-ethyl-4-(4'-tert-butylphenyl)indenyl)zirconium dichloride
methylethylidenoxy(L)(2-ethyl-4-(4'-tert-butylphenyl)indenyl)hafnium dichloride
phenylphosphinediyloxy(L)(2-ethyl-4-(4'-tert-butylphenyl)indenyl)zirconium dichloride
phenylphosphinediyloxy(L)(2-methyl-4-(4'-tert-butylphenyl)indenyl zirconium dichloride
phenylphosphinediyloxy(L)(2-ethyl-4-(4'-tert-butylphenyl)indenyl)zirconium dichloride
dimethylsilanyloxy(L)(2-methyl-4-azapentalene)zirconium dichloride
dimethylsilanyloxy(L)(2-methyl-5-azapentalene)zirconium dichloride
dimethylsilanyloxy(L)(2-methyl-6-azapentalene)zirconium dichloride
dimethylsilanyloxy(L)(2-methyl-N-phenyl-4-azapentalene)zirconium dichloride
dimethylsilanyloxy(L)(2-methyl-N-phenyl-5-azapentalene)zirconium dichloride
dimethylsilanyloxy(L)(2-methyl-N-phenyl-6-azapentalene)zirconium dichloride
dimethylsilanyloxy(L)(2,5-dimethyl-4-azapentalene)zirconium dichloride
dimethylsilanyloxy(L)(2,5-dimethyl-6-azapentalene)zirconium dichloride
dimethylsilanyloxy(L)(2,5-dimethyl-N-phenyl-4-azapentalene)zirconium dichloride
dimethylsilanyloxy(L)(2,5-dimethyl-N-phenyl-6-azapentalene)zirconium dichloride
dimethylsilanyloxy(L)(2-methyl-4-thiapentalene) zirconium dichloride
dimethylsilanyloxy(L)(2-methyl-5-thiapentalene)zirconium dichloride
dimethylsilanyloxy(L)(2-methyl-6-thiapentalene)zirconium dichloride
dimethylsilanyloxy(L)(2,5-dimethyl-4-thiapentalene)zirconium dichloride
dimethylsilanyloxy(L)(2,5-dimethyl-4-thiapentalene)zirconium dichloride
dimethylsilanyloxy(L)(2-methyl-4-oxapentalene)zirconium dichloride dimethylsilanyloxy(L)(2-methyl-5-oxapentalene)zirconium dichloride
dimethylsilanyloxy(L)(2-methyl-6-oxapentalene)zirconium dichloride
dimethylsilanyloxy(L)(2,5-dimethyl-4-oxapentalene) zirconium dichloride
dimethylsilanyloxy(L)(2,5-dimethyl-6-oxapentalene) zirconium dichloride Illustrative but nonlimiting examples of L are:

(butylbenzylidene)-N-phenylaminato, (butylbenzylidene)-(N-2,6-diisopropylphenyl)aminato, (butylbenzylidene-N-cyclohexyl)aminato, (butylbenzyliden)-N-tolylaminato, (butylbenzylidene)-N-isopropylaminato, (butylbenzylidene)-N-tert-butylaminato, (butylbenzylidene)-N-cyclopentylaminato, (butylbenzylidene)-N-methylaminato, (butylbenzylidene)-N-ethylaminato, (butylbenzylidene)-N-(2,4,6-trimethylphenyl)aminato, (butylbenzylidene)-N-(4-tert-butylphenyl)aminato, (butylbenzylidene)-N-(2,4,6-triphenylphenyl)aminato, (butylbenzylidene)-N-(4-isopropylphenyl)aminato, (butylbenzylidene)-N-(2,6-dimethylphenyl)aminato, (butylbenzylidene)-N-(4-butylphenyl)aminato, (butylbenzylidene)-N-(2,6-diphenylphenyl)aminato, (butylbenzylidene)-N-(2,4,6-tripropylphenyl)aminato, (butylbenzylidene)-N-(2,4,6-trifluorophenyl)aminato, (butylbenzylidene)-N-(2,3,4,5,6-pentafluorophenyl)aminato, (butylbenzylidene)-N-(2,3,4,5,6-pentachlorophenyl)aminato, (butylbenzylidene)-N-(2,3,4,5,6-pentabromophenyl)aminato, (butylbenzylidene)-N-(2,4,6-trimethoxyphenyl)aminato, (butylbenzylidene)-N-(2,5,6-trimethoxyphenyl)aminato, (butylbenzylidene)-N-(2,6-dimethoxyphenyl)aminato, (butylbenzylidene)-N-(2,4,6-trichlorophenyl)aminato, (butylbenzylidene)-N-(2,4,6-trimethylsilylphenyl)aminato, (butylbenzylidene)-N-(2,4,6-trihydroxyphenyl)aminato, (butylbenzylidene)-N-(2,4,6-trinitrosophenyl)aminato, (butylbenzylidene)-N-(2,4,6-triisopropylphenyl)aminato, (butylbenzylidene)-N-(2,6-diisopropylphenyl)aminato, (butylbenzylidene)-N-(3,5-diisopropylphenyl)aminato, (butylbenzylidene)-N-(2,6-dicyanatophenyl)aminato, (3,5-di-tert-butylbutylbenzylidene)-N-phenylaminato, (3,5-di-tert-butylbutylbenzylidene)-(N-2,6-diisopropylphenyl)aminato, (3,5-di-tert-butyl-butylbenzylidene-N-cyclohexyl)aminato, (3,5-di-tert-butylbutylbenzylidene)-N-tolylaminato, (3,5-di-tert-butylbutylbenzylidene)-N-isopropylaminato, (3,5-di-tert-butylbutylbenzylidene)-N-tert-butylaminato, (3,5-di-tert-butylbutylbenzylidene)-N-cyclopentylaminato, (3,5-di-tert-butylbutylbenzylidene)-N-methylaminato, (3,5-di-tert-butylbutylbenzylidene)-N-ethylaminato, (3,5-di-tert-butylbutylbenzylidene)-N-(2-4,6-trimethylphenyl)aminato, (3,5-di-tert-butylbutylbenzylidene)-N-(4-tert-butylphenyl)aminato, (3,5-di-tert-butylbutylbenzylidene)-N-(2,4,6-triphenylphenyl)aminato, (3,5-di-tert-butylbutylbenzylidene)-N-(4-isopropylphenyl)aminato, (3,5-di-tert-butylbutylbenzylidene)-N-(2,6-dimethylphenyl)aminato, (3,5-di-tert-butylbutylbenzylidene)-N-(4-butylphenyl)aminato, (3,5-di-tert-butylbutylbenzylidene)-N-(2,6-diphenylphenyl)aminato, (3,5-di-tert-butylbutylbenzylidene)-N(2,4,6-tripropylphenyl)aminato, (3,5-di-tert-butylbutylbenzylidene)-N-(2,4,6-trifluorophenyl)aminato, (3,5-di-tert-butylbutylbenzylidene)-N-(2,3,4,5,6-pentafluorophenyl)aminato, (3,5-di-tert-butylbutylbenzylidene)-N-(2,3,4,5,6-pentachlorophenyl)aminato, (3,5-di-tert-butylbutylbenzylidene)-N-(2,3,4,5,6-pentabromophenyl)aminato, (3,5-di-tert-butylbutylbenzylidene)-N-(2,4,6-trimethoxyphenyl)aminato, (3,5-di-tert-butylbutylbenzylidene)-N-(2,5,6-trimethoxyphenyl)aminato, (3,5-di-tert-butylbutylbenzylidene)-N-(2,6-dimethoxyphenyl) aminato, (3,5-di-tert-butylbutylbenzylidene)-N-(2,4,6-trichlorophenyl)aminato, (3,5-di-tert-butylbutylbenzylidene)-N-(2,4,6-trimethylsilylphenyl)aminato, (3,5-di-tert-butylbutylbenzylidene)-N-(2,4,6-trihydroxyphenyl) aminato, (3,5-di-tert-butylbutylbenzylidene)-N-(2,4,6-trinitrosophenyl) aminato, (3,5-di-tert-butylbutylbenzylidene)-N-(2,4,6-triisopropylphenyl)aminato, (3,5-di-tert-butylbutylbenzylidene)-N-(2,6-diisopropylphenyl) aminato, (3,5-di-tert-butylbutylbenzylidene)-N-(3,5-diisopropylphenyl)aminato, (3,5-di-tert-butylbutylbenzylidene)-N-(2,6-dicyanatophenyl)aminato, (3,5-diisopropylbutylbenzylidene)-N-phenylaminato, (3,5-diisopropylbutylbenzylidene)-(N-2,6-diisopropylphenyl)aminato, (3,5-diisopropylbutylbenzylidene-N-cyclohexyl)aminato, (3,5-diisopropylbutylbenzylidene)-N-tolylaminato, (3,5-diisopropylbutylbenzylidene)-N-isopropylaminato, (3,5-diisopropylbutylbenzylidene)-N-tert-butylaminato, (3,5-diisopropylbutylbenzylidene)-N-cyclopentylaminato, (3,5-diisopropylbutylbenzylidene)-N-methylaminato, (3,5-diisopropylbutylbenzylidene)-N-ethylaminato, (3,5-diisopropylbutylbenzylidene)-N-(2,4,6-trimethylphenyl)aminato, (3,5-diisopropylbutylbenzylidene)-N-(4-tert-butylphenyl)aminato, (3,5-diisopropylbutylbenzylidene)-N-(2,4,6-triphenylphenyl)aminato, (3,5-diisopropylbutylbenzylidene)-N-(4-isopropylphenyl)aminato, (3,5-diisopropylbutylbenzylidene)-N-(2,6-dimethylphenyl)aminato, (3,5-diisopropylbutylbenzylidene)-N-(4-butylphenyl)aminato, (3,5-diisopropylbutylbenzylidene)-N-(2,6-diphenylphenyl)aminato, (3,5-diisopropylbutylbenzylidene)-N-(2,4,6-tripropylphenyl)aminato, (3,5-diisopropylbutylbenzylidene)-N-(2,4,6-trifluorophenyl)aminato, (3,5-diisopropylbutylbenzylidene)-N-(2,3,4,5,6-pentafluorophenyl)aminato, (3,5-diisopropylbutylbenzylidene)-N-(2,3,4,5,6-pentachlorophenyl)aminato, (3,5-diisopropylbutylbenzylidene)-N-(2,3,4,5,6-pentabromophenyl)aminato, (3,5-diisopropylbutylbenzylidene)-N-(2,4,6-trimethoxyphenyl)aminato, (3,5-diisopropylbutylbenzylidene)-N-(2,5,6-trimethoxyphenyl)aminato, (3,5-diisopropylbutylbenzylidene)-N-(2,6-dimethoxyphenyl)aminato, (3,5-diisopropylbutylbenzylidene)-N-(2,4,6-trichlorophenyl)aminato, (3,5-diisopropylbutylbenzylidene)-N-(2,4,6-trimethylsilylphenyl)aminato, (3,5-diisopropylbutylbenzylidene)-N-(2,4,6-trihydroxyphenyl)aminato, (3,5-diisopropylbutylbenzylidene)-N-(2,4,6-trinitrosophenyl)aminato, (3,5-diisopropylbutylbenzylidene)-N-(2,4,6-triisopropylphenyl)aminato, (3,5-diisopropylbutylbenzylidene)-N-(2,5-diisopropylphenyl)aminato, (3,5-diisopropylbutylbenzylidene)-N-3,5-diisopropylphenyl)aminato, (3,5-diisopropylbutylbenzylidene)-N-(2,6-dicyanatophenyl)aminato, (3,5-dimethylbutylbenzylidene)-N-phenylaminato, (3,5-dimethylbutylbenzylidene)-(N-2,6-diisopropylphenyl)aminato, (3,5-dimethylbutylbenzylidene-N-cyclohexyl)aminato, (3,5-dimethylbutylbenzylidene)-N-tolylaminato, (3,5-dimethylbutylbenzylidene)-N-isopropylaminato, (3,5-dimethylbutylbenzylidene)-N-tert-butylaminato, (3,5-dimethylbutylbenzylidene)-N-cyclopentylaminato, (3,5-dimethylbutylbenzylidene)-N-methylaminato, (3,5-dimethylbutylbenzylidene)-N-ethylaminato, (3,5-dimethylbutylbenzylidene)-N-(2,4,6-trimethylphenyl)aminato, (3,5-dimethylbutylbenzylidene)-N-(4-tert-butylphenyl)aminato, (3,5-dimethylbutylbenzylidene)-N-(2,4,6-triphenylphenyl)aminato, (3,5-dimethylbutylbenzylidene)-N-(4- isopropylphenyl)aminato, (3,5-dimethylbutylbenzylidene)-N-(2,6-dimethylphenyl)aminato, (3,5-dimethylbutylbenzylidene)-N-(4-butylphenyl)aminato, (3,5-dimethylbutylbenzylidene)-N-(2,6-diphenylphenyl)aminato, (3,5-dimethylbutylbenzylidene)-N-(2,4,6-tripropylphenyl)aminato, (3,5-dimethylbutylbenzylidene)-N-(2,4,6-trifluorophenyl)aminato, (3,5-dimethylbutylbenzylidene)-N-(2,3,4,5,6-pentafluorophenyl)aminato, (3,5-dimethylbutylbenzylidene)-N-(2,3,4,5,6-pentachlorophenyl)aminato, (3,5-dimethylbutylbenzylidene)-N-(2,3,4,5,6-pentabromophenyl)aminato, (3,5-dimethylbutylbenzylidene)-N-(2,4,6-trimethoxyphenyl)aminato, (3,5-dimethylbutylbenzylidene)-N-(2,5,6-trimethoxyphenyl)aminato, (3,5-dimethylbutylbenzylidene)-N-(2,6-dimethoxyphenyl)aminato, (3,5-dimethylbutylbenzylidene)-N-(2,4,6-trichlorophenyl)aminato, (3,5-dimethylbutylbenzylidene)-N-(2,4,6-trimethsilylphenyl)aminato, (3,5-dimethylbutylbenzylidene)-N-(2,4,6-trihydroxyphenyl)aminato, (3,5-dimethylbutylbenzylidene)-N-(2,4,6-trinitrosophenyl)aminato, (3,5-dimethylbutylbenzylidene)-N-(2,4,6-triisopropylphenyl)aminato, (3,5-dimethylbutylbenzylidene)-N-(2,6-dimethylphenyl)aminato, (3,5-dimethylbutylbenzylidene)-N-(3,5-dimethylphenyl)aminato, (3,5-dimethylbutylbenzylidene)-N-(2,6-dicyanatophenyl)aminato, (4,5-diisopropylbutylbenzylidene)-N-phenylaminato, (4,5-diisopropylbutylbenzylidene)-(N-2,6-diisopropylphenyl)aminato, (4,5-diisopropylbutylbenzylidene-N-cyclohexyl)aminato, (4,5-diisopropylbutylbenzylidene)-N-tolylaminato, (4,5-diisopropylbutylbenzylidene)-N-isopropylaminato, (4,5-diisopropylbutylbenzylidene)-N-tert-butylaminato, (4,5-diisopropylbutylbenzylidene)-N-cyclopentylaminato, (4,5-diisopropylbutylbenzylidene)-N-methylaminato, (4,5-diisopropylbutylbenzylidene)-N-ethylaminato, (4,5-diisopropylbutylbenzylidene)-N-(2,4,6-trimethylphenyl)aminato, (4,5-diisopropylbutylbenzylidene)-N-(4-tert-butylphenyl)aminato, (4,5-diisopropylbutylbenzylidene)-N-(2,4,6-triphenylphenyl)aminato, (4,5-diisopropylbutylbenzylidene)-N-(4-isopropylphenyl)aminato, (4,5-diisopropylbutylbenzylidene)-N-(2,6-dimethylphenyl)aminato, (4,5-diisopropylbutylbenzylidene)-N-(4-butylphenyl)aminato, (4,5-diisopropylbutylbenzylidene)-N-(2,6-diphenylphenyl)aminato, (4,5-diisopropylbutylbenzylidene)-N-(2,4,6-tripropylphenyl)aminato, (4,5-diisopropylbutylbenzylidene)-N-(2,4,6-trifluorophenyl)aminato, (4,5-diisopropylbutylbenzylidene)-N-(2,3,4,5,6-pentafluorophenyl)aminato, (4,5-diisopropylbutylbenzylidene)-N-(2,3,4,5,6-pentachlorophenyl)aminato, (4,5-diisopropylbutylbenzylidene)-N-(2,3,4,5,6-pentabromophenyl)aminato, (4,5-diisopropylbutylbenzylidene)-N-(2,4,6-trimethoxyphenyl)aminato, (4,5-diisopropylbutylbenzylidene)-N-(2,5,6-trimethoxyphenyl)aminato, (4,5-diisopropylbutylbenzylidene)-N-(2,6-dimethoxyphenyl)aminato, (4,5-diisopropylbutylbenzylidene)-N-(2,4,6-trichlorophenyl)aminato, (4,5-diisopropylbutylbenzylidene)-N-(2,4,6-trimethsilylphenyl)aminato, (4,5-diisopropylbutylbenzylidene)-N-(2,4,6-trihydroxyphenyl)aminato, (4,5-diisopropylbutylbenzylidene)-N-(2,4,6-trinitrosophenyl)aminato, (4,5-diisopropylbutylbenzylidene)-N-(2,4,6-triisopropylphenyl)aminato, (4,5-diisopropylbutylbenzylidene)-N-(2,6-diisopropylphenyl)aminato, (4,5-diisopropylbutylbenzylidene)-N-(3,5-diisopropylphenyl)aminato, (4,5-diisopropylbutylbenzylidene)-N-(2,6-dicyanatophenyl)aminato, (4,5-di-tert-butylbutylbenzylidene)-N-phenylaminato, (4,5-di-tert-butylbutylbenzylidene)-(N-2,6-diisopropylphenyl)aminato, (4,5-di-tert-butylbutylbenzylidene-N-cyclohexyl)aminato, (3,5-di-tert-butylbutylbenzylidene)-N-tolylaminato, (4,5-di-tert-butylbutylbenzylidene)-N-isopropylaminato, (4,5-di-tert-butylbutylbenzylidene)-N-tert-butylaminato, (4,5-di-tert-butylbutylbenzylidene)-N-cyclopentylaminato, (4,5-di-tert-butylbutylbenzylidene)-N-methylaminato, (4,5-di-tert-butylbutylbenzylidene)-N-ethylaminato, (4,5-di-tert-butylbutylbenzylidene)-N-(2,4,6-trimethylphenyl)aminato, (4,5-di-tert-butylbutylbenzylidene)-N-(4-tert-butylphenyl)aminato, (4,5-di-tert-butylbutylbenzylidene)-N-(2,4,6-triphenylphenyl)aminato, (4,5-di-tert-butylbutylbenzylidene)-N-(4-isopropylphenyl)aminato, (4,5-di-tert-butylbutylbenzylidene)-N-(2,6-dimethylphenyl)aminato, (4,5-di-tert-butylbutylbenzylidene)-N-(4-butylphenyl)aminato, (4,5-di-tert-butylbutylbenzylidene)-N-(2,6-diphenylphenyl)aminato, (4,5-di-tert-butylbutylbenzylidene)-N-(2,4,6-tripropylphenyl)aminato, (4,5-di-tert-butylbutylbenzylidene)-N-(2,4,6-trifluorophenyl)aminato, (4,5-di-tert-butylbutylbenzylidene)N-(2,3,4,5,6-pentafluorophenyl)aminato, (4,5-di-tert-butylbutylbenzylidene)-N-(2,3,4,5,6-pentachlorophenyl)aminato, (4,5-di-tert-butylbutylbenzylidene)-N-(2,3,4,5,6-pentabromophenyl)aminato, (4,5-di-tert-butylbutylbenzylidene)-N-(2,4,6-trimethoxyphenyl)aminato, (4,5-di-tert-butylbutylbenzylidene)-N-(2,5,6-trimethoxyphenyl)aminato, (4,5-di-tert-butylbutylbenzylidene)-N-(2,6-dimethoxyphenyl)aminato, (4,5-di-tert-butylbutylbenzylidene)-N-(2,4,6-trichlorophenyl)aminato, (4,5-di-tert-butylbutylbenzylidene)-N-(2,4,6-trimethsilylphenyl)aminato, (4,5-di-tert-butylbutylbenzylidene)-N-(2,4,6-trihydroxyphenyl)aminato, (4,5-di-tert-butylbutylbenzylidene)-N-(2,4,6-trinitrosophenyl)aminato, (4,5-di-tert-butylbutylbenzylidene)-N-(2,4,6-triisopropylphenyl)aminato, (4,5-di-tert-butylbutylbenzylidene)-N-(2,6-diisopropylphenyl)aminato, (4,5-di-tert-butylbutylbenzylidene)-N-(3,5-diisopropylphenyl)aminato, (4,5-di-tert-butylbutylbenzylidene)-N-(2,6-dicyanatophenyl)aminato.

Further examples of compounds according to the present invention are the abovementioned organometallic compounds in which the zirconium fragment "zirconium dichloride" is replaced by zirconium monochloride mono(2,4-di-tert-butylphenoxide)
zirconium monochloride mono(2,6-di-tert-butylphenoxide)
zirconium monochloride mono(3,5-di-tert-butylphenoxide)
zirconium monochloride mono(2,6-di-sec-butylphenoxide)
zirconium monochloride mono(2,4-di-methylphenoxide)
zirconium monochloride mono(2,3-di-methylphenoxide)
zirconium monochloride mono(2,5-dimethylphenoxide)
zirconium monochloride mono(2,6-dimethylphenoxide)
zirconium monochloride mono(3,4-dimethylphenoxide)
zirconium monochloride mono(3,5-dimethylphenoxide)
zirconium monochloride monophenoxide
zirconium monochloride mono(2-methylphenoxide)
zirconium monochloride mono(3-methylphenoxide)
zirconium monochloride mono(4-methylphenoxide)
zirconium monochloride mono(2-ethylphenoxide)
zirconium monochloride mono(3-ethylphenoxide)
zirconium monochloride mono(4-ethylphenoxide)
zirconium monochloride mono(2-sec-butylphenoxide)
zirconium monochloride mono(2-tert-butylphenoxide)
zirconium monochloride mono(3-tert-butylphenoxide)
zirconium monochloride mono(4-sec-butylphenoxide)
zirconium monochloride mono(4-tert-butylphenoxide)

zirconium monochloride mono(2-isopropyl-5-methylphenoxide)
zirconium monochloride mono(4-isopropyl-3-methylphenoxide)
zirconium monochloride mono(5-isopropyl-2-methylphenoxide)
zirconium monochloride mono(5-isopropyl-3-methylphenoxide)
zirconium monochloride mono(2,4-bis(2-methyl-2-butyl)phenoxide)
zirconium monochloride mono(2,6-di-tert-butyl-4-methylphenoxide)
zirconium monochloride mono(4-nonylphenoxide)
zirconium monochloride mono(1-naphtholate)
zirconium monochloride mono(2-naphtholate)
zirconium monochloride mono(2-phenylphenoxide)
zirconium monochloride mono(tert-butoxide)
zirconium monochloride mono(N-methylanilide)
zirconium monochloride mono (2-tert-butylanilide)
zirconium monochloride mono (tert-butylamide)
zirconium monochloride mono (diisopropylamide)
monochloromonomethyl zirconium
monochloromonobenzyl zirconium.

The present invention further provides a process for preparing the chemical compound of the formula VII according to the present invention.

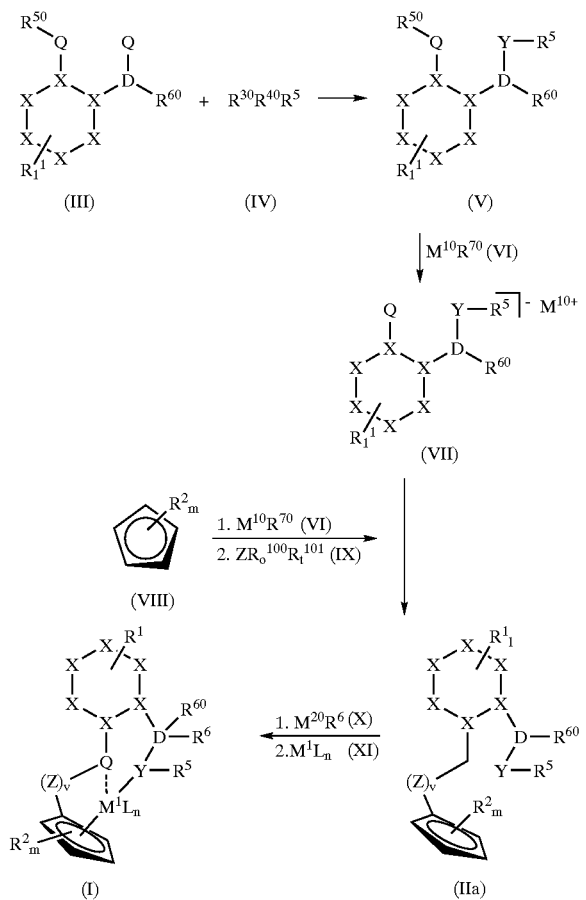

Scheme 1

Here, $M^1$, $R^2$, $R^3$, $R^5$, $R_6$, $R^{60}$, Z, L, m, n, v, X, D, Y are as defined above. In addition:

$R^{30}$, $R^{40}$, R= are identical or different and are each a hydrogen atom or a $C_1$–$C_{12}$-alkyl group, preferably a hydrogen atom, $M^{10}$, $M^{20}$ are each an element of main group I or II of the Periodic Table of the Elements, preferably lithium, sodium, potassium or magnesium, very particularly preferably lithium or sodium, $R^{70}$ is a hydrogen atom or a $C_1$–$C_{20}$ group, preferably a hydrogen atom or $C_1$–$C_{18}$ alkyl such as methyl, ethyl, n-butyl, n-hexyl, tert-butyl, sec-butyl, particularly preferably methyl, n-butyl, sec-butyl, t, o are each an integer from 1 to 4, preferably 2, $R^{100}$, $R^{101}$ are each a halogen atom, in particular chlorine, or an alkyl group such as a $C_1$–$C_{18}$-alkyl group, in particular, ethyl, methyl, tert-butyl.

For this purpose, one or more compounds of the formula (III), which may be dissolved or suspended in a solvent or else be present as such, is/are reacted with one or more compounds of the formula (IV), which can likewise be dissolved or suspended in a solvent or else be present as such. Solvents which may be employed are aliphatic or aromatic hydrocarbons such as n-pentane, isopentane, n-hexane, n-heptane, cyclohexane, isododecane, n-octane, n-nonane, n-decane, petroleum ether, toluene, benzene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, etc., and also ethers, such as diethyl ether, methyl tert-butyl ether, dimethxoyethane, diisopropyl ether, di-n-butyl ether, anisole, methanol, ethanol, isopropanol and butanol or mixtures of these. The addition can be carried out over a period of from 1 minute to 96 hours. Preference is given to addition within from 100 minutes to 36 hours. The temperature of the initial charge during the addition is from −100° C. to 200° C. Preference is given to temperatures of from −80° C. to 150° C. Particular preference is given to temperatures of from 20° C. to 150° C. The temperature is chosen so that at least one reactant is present in a liquid phase. The subsequent reaction temperature is preferably in a temperature range from 20° C. to 150° C. Furthermore, the reaction can be carried out at atmospheric pressure, but can also be carried out at superatmospheric pressure, although this requires appropriate reactors. The stoichiometric ratio in which the compounds of the formulae (III) and (IV) are combined is from 1:1000 to 1:0.01, based on the amount of the compounds of the formula (III) used. Preference is given to a stoichiometric ratio of compounds of the formula (IV) to compounds of the formula (III) used of from 1:100 to 1:0.1. Particular preference is given to a stoichiometric reaction of the compounds of the formulae (III) and (IV).

Illustrative but nonlimiting examples of compounds of the formula (III) according to the present invention are:

3,5-di-tert-butyl-2-hydroxybenzaldehyde, 1-{3,5-di(tert-butyl)-2-hydroxyphenyl}ethan-1-one, 2-hydroxybenzophenone, 2-hydroxybenzaldehyde, 1-{2-hydroxyphenyl}-ethane-1-one, 3,5-diisopropyl-2-hydroxybenzaldehyde, 3,5-ditrimethysilyl-2-hydroxybenzaldehyde, 3,5-dimethyl-2-hydroxybenzaldehyde, 3,5-diethyl-2-hydroxybenzaldehyde, 3,5-di-n-propyl-2-hydroxybenzaldehyde, 3,5-di-n-butyl-2-hydroxybenzaldehyde, 3,5-diphenyl-2-hydroxybenzaldehyde, 3,5-ditolyl-2-hydroxybenzaldehyde, 3,5-dinaphthyl-2-hydroxybenzaldehyde, 3,5-diadamantyl-2-hydroxybenzaldehyde, 3,5-dinorbornyl-2-hydroxybenzaldehyde, 3,5-difluoro-2-hydroxybenzaldehyde, 3,5-dichloro-2-hydroxybenzaldehyde, 4,6-diisopropyl-2-hydroxybenzaldehyde, 4,6-ditrimethylsilyl-2-hydroxybenzaldehyde, 4,6-dimethyl-2-hydroxybenzaldehyde, 4,6-diethyl-2-hydroxybenzaldehyde, 4,6-di-n-propyl-2-hydroxybenzaldehyde, 4,6-di-n-butyl-2-hydroxybenzaldehyde, 4,6-diphenyl-2- hydroxybenzaldehdye, 4,6-ditolyl-2-hydroxybenzaldehyde, 4,6-dinaphthyl-2-hydroxybenzaldehyde, 4,6-diadamantyl-2-hydroxybenzaldehyde, 4,6-dinorbornyl-2-hydroxybenzaldehyde, 4,6-difluoro-2-hydroxybenzaldehyde, 4,6-dichloro-2-hydroxybenzaldehyde, 3,6-diisopropyl-2-hydroxybenzaldehyde, 3,6-ditrimethylsilyl-2-hydroxybenzaldhyde, 3,6-dimethyl-2-hydroxybenzaldehyde, 3,6-diethyl-2-hydroxybenzaldehyde, 3,6-di-n-propyl-2-hydroxybenzaldehyde, 3,6-di-n-butyl-2-hydroxybenzaldehyde, 3,6-diphenyl-2-hydroxybenzaldehyde, 3,6-ditolyl-2-hydroxybenzaldehyde, 3,6-dinaphthyl-2-hydroxybenzaldehyde, 3,6-diadamantyl-2-hydroxybenzaldehyde, 3,5-dinorbornyl-2-hydroxybenzaldehyde, 3,6-difluoro-2-hydroxybenzaldehyde, 3,6-dichloro-2-hydroxybenzaldehyde, 4-isopropyl-2-hydroxybenzaldehyde, 4-trimethylsilyl-2-hydroxybenzaldehyde, 4-methyl-2-hydroxybenzaldehyde, 4-ethyl-2-hydroxybenzaldehyde, 4-n-propyl-2-hydroxybenzaldehyde, 4-n-butyl-2-hydroxybenzaldehyde, 4-phenyl-2-hydroxybenzaldehyde, 4-tolyl-2-hydroxybenzaldehyde, 4-naphthyl-2-hydroxybenzaldehyde, 4-adamanthyl-2-hydroxybenzaldehyde, 4-norbornyl-2-hydroxybenzaldehyde, 4-fluoro-2-hydroxybenzaldehyde, 4-chloro-2-hydroxybenzaldehyde, 4-isopropyl-2-hydroxybenzaldehyde, 3-trimethylsilyl-2-hydroxybenzaldehyde, 3-methyl-2-hydroxybenzaldehyde, 3-ethyl-2-hydroxybenzaldehyde, 3-n-propyl-2-hydroxybenzaldehyde, 3-n-butyl-2-hydroxybenzaldehyde, 3-phenyl-2-hydroxybenzaldehyde, 3-tolyl-2-hydroxybenzaldehyde, 3-naphthyl-2-hydroxybenzaldehyde, 3-adamanthyl-2-hydroxybenzaldehyde, 3-norbornyl-2-hydroxybenzaldehyde, 3-fluoro-2-hydroxybenzaldehyde, 3-chloro-2-hydroxybenzaldehyde, 5-isopropyl-2-hydroxybenzaldehyde, 5-trimethylsilyl-2-hydroxybenzaldehyde, 5-methyl-2-hydroxybenzaldehyde, 5-ethyl-2-hydroxybenzaldehyde, 5-n-propyl-2-hydroxybenzaldehyde, 5-n-butyl-2-hydroxybenzaldehyde, 5-phenyl-2-hydroxybenzaldehyde, 5-tolyl-2-hydroxybenzaldehyde, 5-naphthyl-2-hydroxybenzaldehyde, 5-adamanthyl-2-hydroxybenzaldehyde, 5-norbornyl-2-hydroxybenzaldehyde, 5-fluoro-2-hydroxybenzaldehyde, 5-chloro-2-hydroxybenzaldehyde, 4-isopropyl-2-hydroxybenzaldehyde, 6-trimethylsilyl-2-hydroxybenzaldehyde, 6-methyl-2-hydroxybenzaldehyde, 6-ethyl-2-hydroxybenzaldehyde, 6-n-propyl-2-hydroxybenzaldehyde, 6-n-butyl-2-hydroxybenzaldehyde, 6-phenyl-2-hydroxybenzaldehyde, 6-tolyl-2-hydroxybenzaldehyde, 6-naphthyl-2-hydroxybenzaldehyde, 6-adamanthyl-2-hydroxybenzaldehyde, 6-norbornyl-2-hydroxybenzaldehyde, 6-fluoro-2-hydroxybenzaldehyde, 6-chloro-2-hydroxybenzaldehyde, 3,4,5,6-tetrafluoro-2-hydroxybenzaldehyde, 3,4,5,6-tetrachloro-2-hydroxybenzaldehyde, 3,5,6-trifluoro-2-hydroxybenzaldehyde, 3,5,6-trichloro-2-hydroxybenzaldehyde, 1-{3,5-di(tert-butyl)-2-hydroxyphenyl}propan-1-one, 1-{3,5-di(tert-butyl)-2-hydroxyphenyl}pentan-1-one, 1-{3,5-di(tert-butyl)-2-hydroxyphenyl}hexan-1-one, 1-(2-hydroxyphenyl)propan-1-one, 1-(2-hydroxyphenyl)pentan-1-one, 1-(2-hydroxyphenyl)hexan-1-one, 1-{3,5-(di(tert-butyl 2-hydroxyphenyl}pyridin-1-one.

Illustrative but nonlimiting examples of compounds of the formula (IV) according to the present invention are:

cyclohexylamine, isopropylamine, benzylamine, p-toluidine, methylamine, propylamine, cyclopentylamine, cycloheptylamine, cyclooctylamine, nonylamine, ethylamine, butylamine, tert-butylamine, phenylamine, isobutylamine, pentylamine, hexylamine, octylamine, heptylamine, xylylamine, naphthylamine sec-butylamine, adamantylamine, norbornylamine, pentafluorophenylamine, pentachlorophenylamine, amino pyridine, amino pyrrolidine.

In the next step, one or more compounds of the formula (V) can be placed in a reaction vessel. The compounds can either be dissolved or suspended in a solvent, or else can be present as such. Solvents which may be employed are aliphatic or aromatic hydrocarbons such as n-pentane, isopentane, n-hexane, n-heptane, cyclohexane, isododecane, n-octane, n-nonane, n-decane, petroleum ether, toluene, benzene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, etc., and also ethers such as diethyl ether, methyl tert-butyl ether, dimethoxyethane, diisopropyl ether, di-n-butyl ether, anisole, methanol, ethanol, isopropanol and butanol or mixtures of these. The initial charge is placed in the reaction vessel at from −100° C. to 300° C., preferably from −80° C. to 200° C., particularly preferably from 20° C. to 150° C. The compound of the formula (V) should advantageously be present in a liquid phase.

The addition of one or more compounds of the formula (VI) can subsequently be carried out. These can likewise be dissolved or suspended in a solvent or else can be present as such. Solvents which may be employed are those described above; preference is given to using the same solvent. The addition can be carried out over a period of from 1 minute to 96 hours. Preference is given to addition within from 10 minutes to 16 hours. The temperature of the initial charge during the addition is from −100° C. to 200° C. Preference is given to temperatures of from −80° C. to 150° C. Particular preference is given to temperatures of from 20° C. to 150° C. The temperature is chosen so that at least one reactant is present in the liquid phase. The subsequent reaction temperature is preferably in a temperature range from 20° C. to 150° C. Furthermore, the reaction can be carried out at atmospheric pressure, but it can also be carried out at superatmospheric pressure, although this requires appropriate reactors. The stoichiometric ratio in which the compounds of the formulae (V) and (VI) are combined is, based on the amount of $M^{10}$ in the compounds of the formula (VI) used, from 1:1000 to 1:0.01. Preference is given to a stoichiometric ratio of compounds of the formula (V) to the amount of $M^{10}$ in the compounds of the formula (VI) of from 1:100 to 1:0.1. Particular preference is given to a stoichiometric reaction of the compounds of the formulae (V) and (VI). The result is a compound of the formula (VII).

Illustrative but nonlimiting examples of compounds of the formula VI which can be used according to the present invention are:

lithium diisopropylamide, lithium dimethylamide, lithium diethylamide, lithium diphenylamide, lithium dicyclohexylamide, lithium dibenzylamide, lithium isopropylmethylamide, lithium dibutylamide, lithium di-tert-butylamide, lithium ditolylamide, lithium dicyclopentylamide, lithium dibutylamide, lithium methylethylamide, lithium methylbutylamide, sodium diisopropylamide, sodium dimethylamide, sodium diethylamide, sodium diphenylamide, sodium dicyclohexylamide, sodium dibenzylamide, sodium isopropylmethylamide, sodium dibutylamide, sodium di-tert-butylamide, sodium ditolylamide, sodium dicyclopentylamide, sodium dibutylamide, sodium methylethylamide, sodium methylbutylamide, potassium diisopropylamide, potassium dimethylamide, potassium diethylamide, potassium diphenylamide, potassium dicyclohexylamide, potassium dibenzylamide, potassium isopropylmethylamide, potassium dibutylamide, potassium di-tert-butylamide, potassium ditolylamide, potassium dicyclopentylamide, potassium dibutylamide, potassium methylethylamide and/or potassium methylbutylamide. Further examples are butyllithium, sodium hydride, butyl sodium, dibutylmagnesium, sec-butyllithium.

In the next step, one or more compounds of the formula (VIII) can be placed in a reaction vessel. The compounds can either be dissolved or suspended in a solvent or else can be present as such. Solvents which may be employed are aliphatic or aromatic hydrocarbons such as n-pentane, isopentane, n-hexane, n-heptane, cyclohexane, isododecane, n-octane, n-nonane, n-decane, petroleum ether, toluene, benzene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, etc., and also ethers, such as diethyl ether, methyl tert-butyl ether, dimethoxyethane, diisopropyl ether, di-n-butyl ether, anisole, methanol, ethanol, isopropanol and butanol or mixtures of these. The initial charge is placed in the reaction vessel at temperatures of from −100° C. to 300° C., preferably from −80° C. to 200° C., particularly preferably from 20° C. to 150° C. The compound of the formula (VIII) should advantageously be present in a liquid phase.

The addition of one or more compounds of the formula (VI) can subsequently be carried out. These can likewise be dissolved or suspended in a solvent or else be present as such. Solvents which may be employed are those described above; preference is given to using the same solvent. The addition can be carried out over a period of from 1 minute to 96 hours. Preference is given to addition within from 10 minutes to 16 hours. The temperature of the initial charge during the addition is from −100° C. to 200° C. Preference is given to temperatures of from −80° C. to 150° C. Particular preference is given to temperatures of from 20° C. to 150° C. The temperature should be chosen so that at least one reactant is present in a liquid phase. The subsequent reaction temperature is preferably in a temperature range from 20° C. to 150° C. Furthermore, the reaction can be carried out at atmospheric pressure, but it can also be carried out at superatmospheric pressure, although this requires appropriate reactors. The stoichiometric ratio in which the compounds of the formulae (VIII) and (VI) are combined is, based on the amount of $M^{10}$ in the compounds of the formula (VI) used, from 1:1000 to 1:0.01. Preference is given to a stoichiometric ratio of compounds of the formula (VIII) to the amount of $M^{10}$ in the compounds of the formula (VI) of from 1:100 to 1:0.1. Particular preference is given to a stoichiometric reaction of the compounds of the formulae (VIII) and (VI). The resulting compound is subsequently reacted with a compound of the formula (IX). The reaction conditions and also the solvents used correspond to those described above.

The compound obtained in this way can be isolated or reacted in-situ with the compound of the formula (VII), with the reaction conditions, stoichiometries and order of addition of the individual components and also the solvents used corresponding to those described above.

This reaction gives the ligand system of the formula (II) used according to the present invention. In a final step, one or more compounds of the formula (II) can be placed in a reaction vessel. The compounds can either be dissolved or suspended in a solvent or can be present as such. Solvents which may be employed are aliphatic or aromatic hydrocarbons such as n-pentane, isopentane, n-hexane, n-heptane, cyclohexane, isododecane, n-octane, n-nonane, n-decane, petroleum ether, toluene, benzene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, etc., and also ethers, such as diethyl ether, methyl tert-butyl ether, dimethoxyethane, diisopropyl ether, di-n-butyl ether or mixtures of these. The initial charge is placed in the reaction vessel at from −100° C. to 300° C., preferably from −80° C. to 200° C., in particular from 20° C. to 150° C. The compound of the formula (II) should advantageously be present in a liquid phase.

The addition of one or more compounds of the formula (X) can subsequently be carried out. These can likewise be dissolved or suspended in a solvent or else can be present as such. Solvents which may be employed are those described above; preference is given to using the same solvent. The addition can be carried out over a period of from 1 minute to 96 hours. Preference is given to an addition within from 10 minutes to 16 hours. The temperature of the initial charge during the addition is from −100° C. to 200° C. Preference is given to temperatures of from −80° C. to 150° C. Particular preference is given to temperatures of from 20° C. to 150° C. The temperature is chosen so that at least one reactant is present in a liquid phase. The subsequent reaction temperature is preferably in a temperature range from 20° C. to 150° C. Furthermore, the reaction can be carried out at atmospheric pressure, but it can also be carried out at superatmospheric pressure, although this requires appropriate reactors. The stoichiometric ratio in which the compounds of the formulae (IIa) and (X) are combined is, based on the amount of $M^{20}$ in the compounds of the formula (X) used, from 1:1000 to 1:0.01. Preference is given to a stoichiometric ratio of compounds of the formula (IIa) to the amount of $M^{20}$ in compounds of the formula (X) used of from 1:100 to 1:0.1 Particular preference is given to a stoichiometric reaction of the compounds of the formulae (IIa) and (X). The resulting product can be isolated or used without isolation for the further reaction with the compound of the formula (XI). Here, one or more compounds of the formula (II) can be placed in a reaction vessel. The compounds can either be dissolved or suspended in a solvent or else can be present as such. Solvents which may be employed are those described above.

Illustrative but nonlimiting examples of compounds of the formula (X) which can be used according to the present invention are:

lithium diisopropylamide, lithium dimethylamide, lithium diethylamide, lithium diphenylamide, lithium dicyclohexylamide, lithium dibenzylamide, lithium isopropylmethylamide, lithium dibutylamide, lithium di-tert-butylamide, lithium ditolylamide, lithium dicyclopentylamide, lithium dibutylamide, lithium methylethylamide, lithium methylbutylamide, sodium diisopropylamide, sodium dimethylamide, sodium diethylamide, sodium diphenylamide, sodium dicyclohexylamide, sodium dibenzylamide, sodium isopropylmethylamide, sodium dibutylamide, sodium di-tert-butylamide, sodium ditolylamide, sodium dicyclopentylamide, sodium dibutylamide, sodium methylethylamide, sodium methylbutylamide, potassium diisopropylamide, potassium dimethylamide, potassium diethylamide, potassium diphenylamide, potassium dicyclohexylamide, potassium dibenzylamide, potassium isopropylmethylamide, potassium dibutylamide, potassium di-tert-butylamide, potassium ditolylamide, potassium dicyclopentylamide, potassium dibutylamide, potassium methylethylamide and/or potassium methylbutylamide. Further examples are butyllithium, sodium hydride, butyl sodium, dibutylmagnesium, sec-butyllithium.

The compound of the formula (XI) is subsequently added to one or more compounds of the formula (II). The compounds can either be dissolved or suspended in a solvent or else can be present as such. The reaction conditions and the solvents used correspond to those described above. A compound of the formula (I) is isolated.

As an alternative to this route described in Scheme 1, alternative routes can be employed. These are shown in Schemes 2, 3 and 4. The compounds used correspond to those described above.

Scheme 2

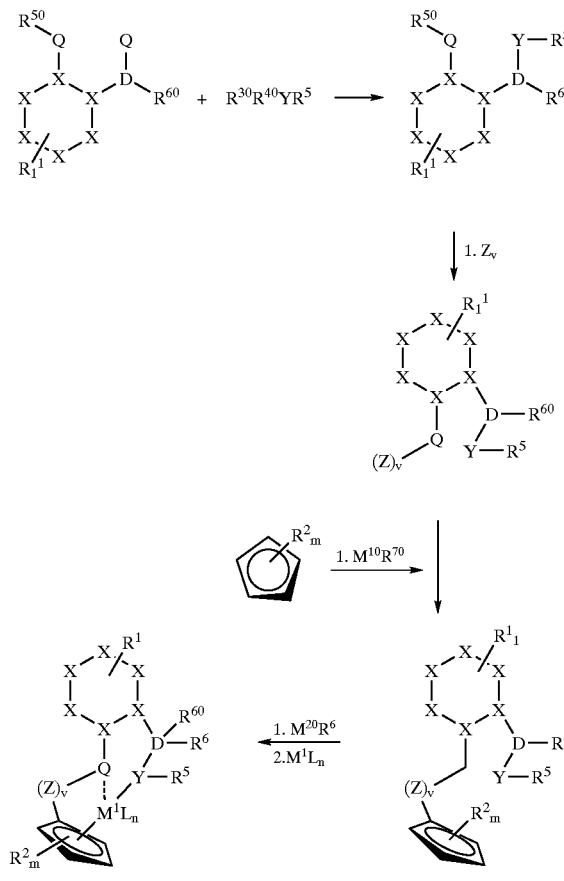

Scheme 3

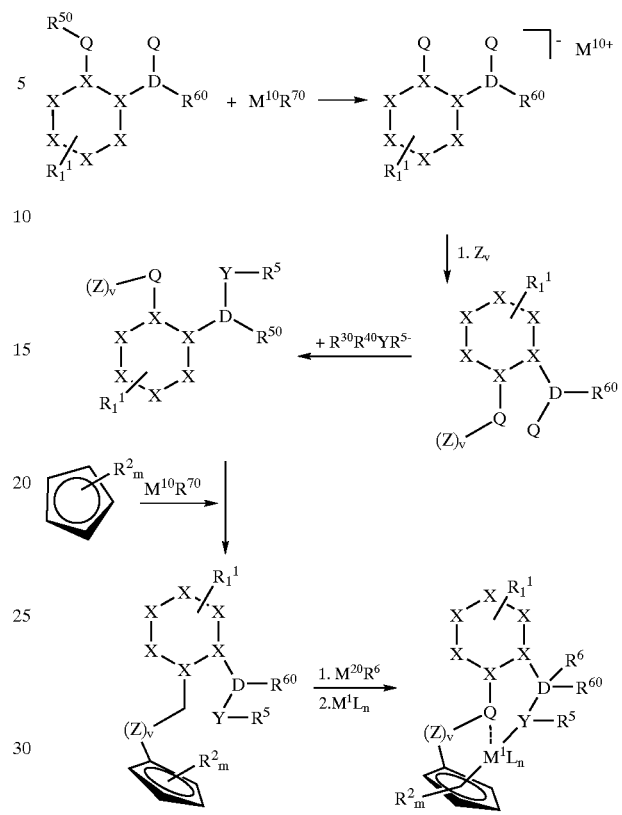

Scheme 4

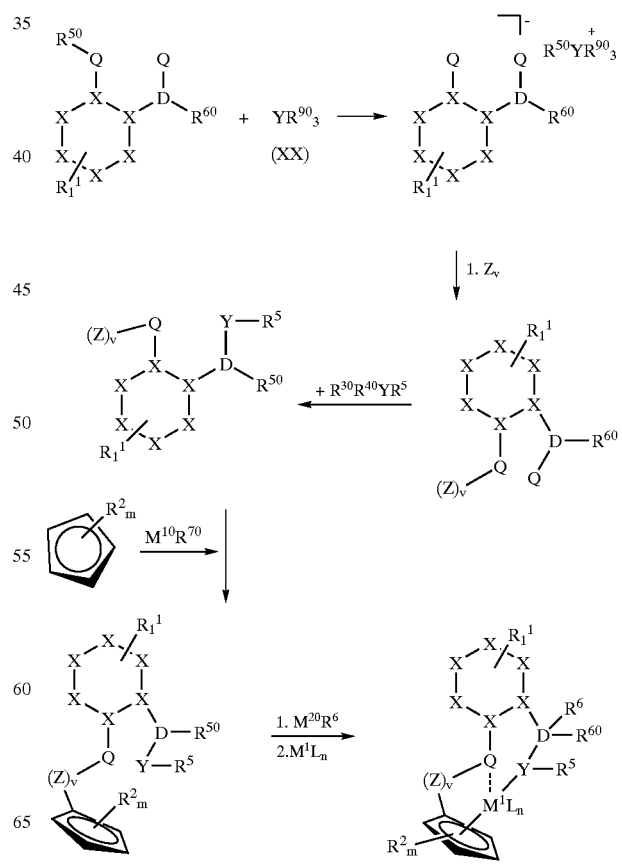

Here, $M^1$, $R^2$, $R^3$, $R^5$, $R^6$, $R^{60}$, Z, L, m, n, v, X, D, Y are as defined above. In addition:

$R^{90}$ are identical or different and are each a hydrogen atom or a $C_1$–$C_{40}$ group such as $C_1$–$C_{20}$-alkyl, $C_2$–$C_{10}$-alkenyl, $C_7$–$C_{40}$-arylalkyl, $C_7$–$C_{40}$-alkylaryl or $C_8$–$C_{40}$arylkenyl, methyl, ethyl, tert-butyl, n-hexyl, isopropyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl.

Illustrative but nonlimiting examples of compounds of the formula (XX) which can be used according to the present invention are:

tricyclohexylamine, triisopropylamine, tribenzylamine, tri-p-tolylamine, trimethylamine, tripropylamine, tricyclopentylamine, tricycloheptenylamine, tricyclooctylamine, trinonylamine, triethylamine, tributylamine, tri-tert-butylamine, triphenylamine, triisobutylamine, tripentylamine, trihexylamine, trioctylamine, triheptylamine, trixylylamine, trinaphthylamine, tri-sec-butylamine, triadamantylamine, trinorbornylamine, tripentafluorophenylamine, tripentachlorophenylamine, tripyridinamine, tripyrrolidinamine.

The present invention further provides a catalyst system comprising the novel chemical compound of the formula (I).

The novel metal complexes of the formula (I) are particularly useful as constituents of catalyst systems for preparing polyolefins by polymerization of at least one olefin in the presence of a catalyst comprising at least one cocatalyst and at least one metal complex.

The cocatalyst which together with a transition metal complex of the formula II according to the present invention forms the catalyst system comprises at least one compound such as an aluminoxane or a Lewis acid or an ionic compound which reacts with an organometallic compound to convert it into a cationic compound.

As aluminoxane, preference is given to using a compound of the formula (XII)

$$(RAlO)_n. \qquad (XII)$$

Further suitable aluminoxanes can be, for example, cyclic as in the formula (XIII)

(XIII)

or linear as in the formula (XIV):

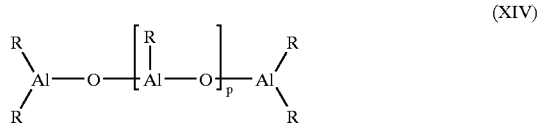

(XIV)

or of the cluster type as in the formula (XV):

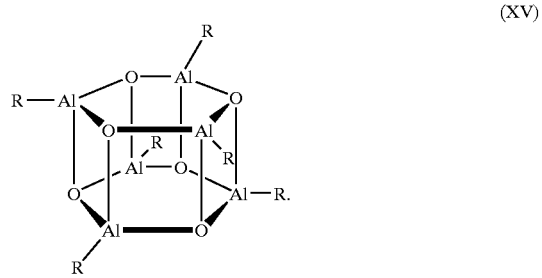

(XV)

Such aluminoxanes are described, for example, in JACS 117 (1995), 6465–74, Organometallics 13 (1994), 2957–2969.

The radicals R in the formulae (XII), (XIII), (XIV) and (XV) may be identical or different and are each a $C_1$–$C_{20}$-hydrocarbon group such as a $C_1$–$C_6$-alkyl group, a $C_6$–$C_{18}$-aryl group, benzyl or hydrogen, and p is an integer from 2 to 50, preferably from 10 to 35. The radicals R are preferably identical and are each methyl, isobutyl, n-butyl, phenyl or benzyl, particularly preferably methyl.

If the radicals R are different, they are preferably methyl and hydrogen, methyl and isobutyl or methyl and n-butyl, with hydrogen or isobutyl or n-butyl preferably being present in a proportion of 0.01–40% of the number of radicals R.

The aluminoxane can be prepared in various ways by known methods. One of the methods is, for example, reacting an aluminum-hydrocarbon compound and/or a hydridoaluminum-hydrocarbon compound with water (gaseous, solid, liquid or bound, for example as water of crystallization) in an inert solvent (e.g. toluene). To prepare an aluminoxane having different alkyl groups R, two different trialkylaluminums ($AlR_3$+$AlR'_3$) corresponding to the desired composition and reactivity are reacted with water (cf. S. Pasynkiewicz, Polyhedron 9 (1990) 429 and EP-A-0,302,424).

Regardless of the method of preparation, all aluminoxane solutions have a varying content of unreacted aluminum starting compound which is present in free form or as adduct.

As Lewis acid, preference is given to using at least one organoboron or organoaluminum compound containing $C_1$–$C_{20}$ groups such as branched or unbranched alkyl or haloalkyl groups, e.g. methyl, propyl, isopropyl, isobutyl, trifluoromethyl, unsaturated groups such as aryl or haloaryl, e.g. phenyl, tolyl, benzyl groups, p-fluorophenyl, 3,5-difluorophenyl, pentachlorophenyl, pentafluorophenyl, 3,4,5-trifluorophenyl and 3,5-di(trifluoromethyl)phenyl.

Examples of Lewis acids are trimethylaluminum, triethylaluminum, triisobutylaluminum, tributylaluminum, trifluoroborane, triphenylborane, tris(4-fluorophenyl)borane, tris(3,5-difluorophenyl)borane, tris(4-fluoromethylphenyl)borane, tris(pentafluorophenyl)borane, tris(tolyl)borane, tris(3,5-dimethylphenyl)borane, tris(3,5-difluorophenyl)borane and/or tris(3,4,5-trifluorophenyl)borane. Particular preference is given to tris(pentafluorophenyl)borane.

As ionic cocatalysts, preference is given to using compounds which have a noncoordinating anion, for example tetrakis(pentafluorophenyl)borate, tetraphenylborate, $SbF_6^-$, $CF_3SO_3^-$ or $ClO_4^-$. As cationic counterions, use is made of protonated Lewis bases such as methylamine, aniline, N,N-dimethylbenzylamine and derivatives thereof, N,N-dimethylcyclohexylamine and derivatives thereof, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline, p-nitro-N,N-dimethylaniline, triethylphosphine, triphenylphosphine, diphenylphosphine, tetrahydrothiophene or triphenylcarbenium.

Examples of such ionic compounds are
triethylammonium tetra(phenyl)borate,
tributylammonium tetra(phenyl)borate,
trimethylammonium tetra(tolyl)borate,
tributylammonium tetra(tolyl)borate,
tributylammonium tetra(pentafluorophenyl)borate,
tributylammonium tetra(pentafluorophenyl)aluminate,
tripropylammonium tetra(dimethylphenyl)borate,
tributylammonium tetra(trifluoromethylphenyl)borate,
tributylammonium tetra(4-fluorophenyl)borate,
N,N-dimethylanilinium tetra(phenyl)borate,
N,N-diethylanilinium tetra(phenyl)borate,
N,N-dimethylanilinium tetrakis(pentafluorophenyl)borate,
N,N-dimethylanilinium tetrakis(pentafluorophenyl)aluminate,
di(propyl)ammonium tetrakis(pentafluorophenyl)borate,
di(cyclohexyl)ammonium tetrakis(pentafluorophenyl)borate,
triphenylphosphonium tetrakis(phenyl)borate,
triethylphosphonium tetrakis(phenyl)borate,
diphenylphosphonium tetrakis(phenyl)borate,
tri(methylphenyl)phosphonium tetrakis(phenyl)borate,
tri(dimethylphenyl)phosphonium tetrakis(phenyl)borate,
triphenylcarbenium tetrakis(pentafluorophenyl)borate,
triphenylcarbenium tetrakis(pentafluorophenyl)aluminate,
triphenylcarbenium tetrakis(phenyl)aluminate,
ferrocenium tetrakis(pentafluorophenyl)borate and/or
ferrocenium tetrakis(pentafluorophenyl)aluminate.

Preference is given to triphenylcarbenium tetrakis(pentafluorophenyl)borate and/or N,N-dimethylanilinium tetrakis(pentafluorophenyl)borate.

It is also possible to use mixtures of at least one Lewis acid and at least one ionic compound.

Further suitable cocatalyst components are borane or carborane compounds such as
7,8-dicarbaundecaborane(13),
undecahydrido-7,8-dimethyl-7,8-dicarbaundecaborane,
dodecahydrido-1-phenyl-1,3-dicarbanonaborane,
tri(butyl)ammonium undecahydrido-8-ethyl-7,9-dicarbaundecaborate,
4-carbanonaborane(14),
bis(tri(butyl)ammonium) nonaborate,
bis(tri(butyl)ammonium) undecaborate,
bis(tri(butyl)ammonium) dodecaborate,
bis(tri(butyl)ammonium) decachlorodecaborate,
tri(butyl)ammonium 1-carbadecaborate,
tri(butyl)ammonium 1-carbadodecaborate,
tri(butyl)ammonium 1-trimethylsilyl-1-carbadecaborate,
tri(butyl)ammonium bis(nonahydrido-1,3-dicarbanonaborato)cobaltate(III),
tri(butyl)ammonium bis(undecahydrido-7,8-dicarbaundecaborato)ferrate(III).

Further useful cocatalyst systems are combinations of at least one of the abovementioned amines and a support with organoelement compounds as are described in WO 99/40129.

Preferred constituents of these cocatalyst systems are the compounds of the formulae (A) and (B):

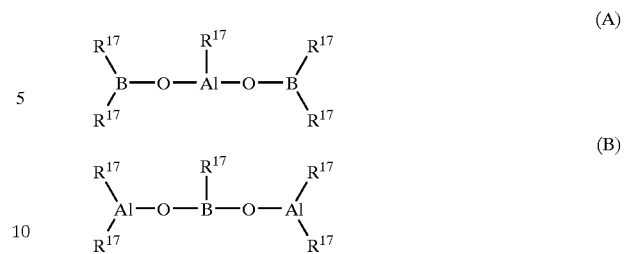

where
A$^{17}$ is a hydrogen atom, a halogen atom, a $C_1$–$C_{40}$ group, in particular $C_1$–$C_{20}$-alkyl, $C_1$–$C_{20}$haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl or $C_7$–$C_{40}$-haloalkylaryl. R$^{17}$ can also be an —OSiR$^{18}{}_3$ group, where R$^{18}$ are identical or different and are as defined for R$^{17}$.

Further preferred cocatalysts are in general compounds which are formed by reaction of at least one compound of the formula (C) and/or (D) and/or (E) with at least one compound of the formula (F):

$R^{17}{}_v B\!-\!(DR\text{-}80)_s$ (C)

$R^{17}{}_2 B\!-\!X^1\!-\!BR^{17}{}_2$ (D)

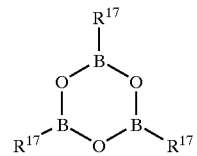 (E)

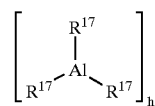 (F)

where
R$^{80}$ can be a hydrogen atom or a boron-free $C_1$–$C_{40}$ group such as $C_1$–$C_{20}$-alkyl, $C_6C_{20}$-aryl, $C_7$–$C_{40}$-arylalkyl, $C_7$–$C_{40}$-alkylaryl and
R$^{17}$ is as defined above,
X$^1$ is an element of main group VI of the Periodic Table of the Elements or an NR group, where R is a hydrogen atom or a $C_1$–$C_{20}$-hydrocarbon radical such as $C_1$–$C_{20}$-alkyl or $C_1$–$C_{20}$-aryl,
D is an element of main group VI of the Periodic Table of the Elements or an NR group, where R is a hydrogen atom or a $C_1$–$C_{20}$-hydrocarbon radical such as $C_1$–$C_{20}$-alkyl or $C_1$–$C_{20}$-aryl,
v is an integer from 0 to 3,
s is an integer from 0 to 3,
h is an integer from 1 to 10,
B is boron,
Al is aluminum.

If desired, the organoelement compounds are combined with an organometallic compound of the formulae XII to XV and/or XVI [M$^{40}$R$^{19}{}_b]_d$, where M$^{40}$ is an element of main group I, II or III of the Periodic Table of the Elements, R$^{19}$ are identical or different and are each a hydrogen atom, a halogen atom, a $C_1$–$C_{40}$ group, in particular $C_1$–$C_{20}$-alkyl, $C_6$–$C_{40}$-aryl, $C_7$–$C_{40}$-arylalkyl or $C_7$–$C_{40}$-alkylaryl, b is an integer from 1 to 3 and d is an integer from 1 to 4.

Examples of cocatalytically active compounds of the formulae A and B are:

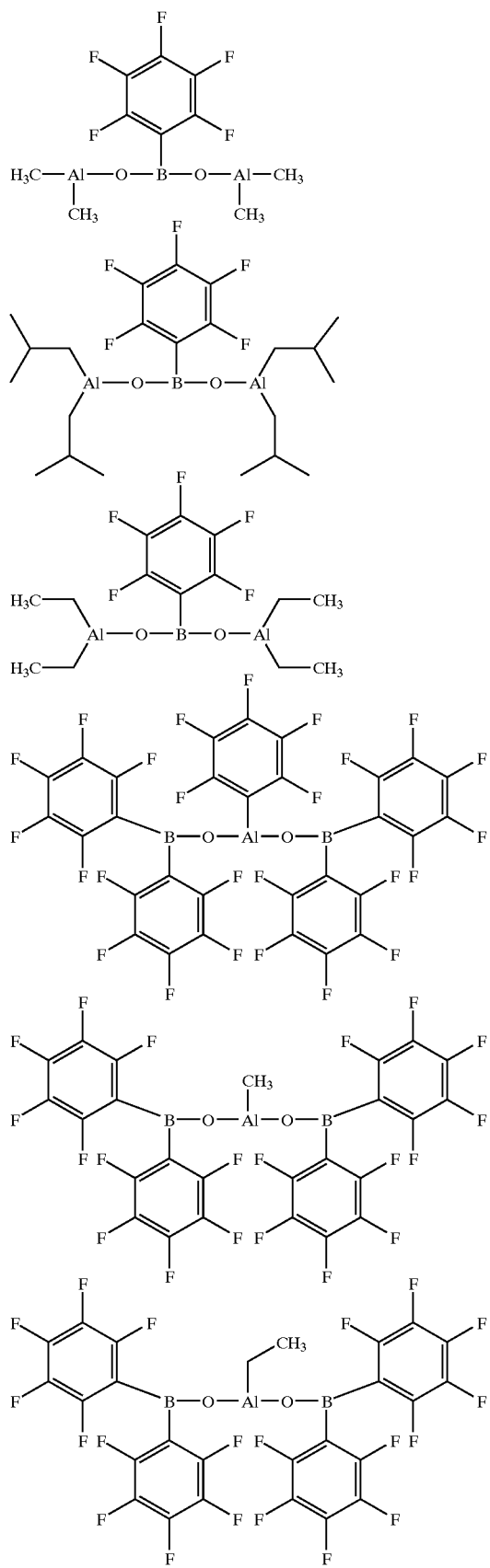

The organometallic compounds of the formula XVI are preferably uncharged Lewis acids in which $M^{40}$ is lithium, magnesium and/or aluminum, in particular aluminum. Examples of preferred organometallic compounds of the formula XII are trimethylaluminum, triethylaluminum, triisopropylaluminum, trihexylaluminum, trioctylaluminum, tri-n-butylaluminum, tri-n-propylaluminum, triisoprenylaluminum, dimethylaluminuhm monochloride, diethylaluminum monochloride, diisobutylaluminum monochloride, methylaluminum sesquichloride, ethylaluminum sesquichloride, dimethylaluminum hydride, diethylaluminum hydride, diisopropylaluminum hydride, dimethylaluminum trimethylsiloxide, dimethylaluminum triethylsiloxide, phenylalane, pentafluorophenylalane and o-tolylalane.

Further useful cocatalysts, which may be in unsupported or supported form, are the compounds mentioned in EP-A-924233, DE-A-19622207, EP-A-601830, EP-A-824112, EP-A-824113, EP-A-811627, WO97/11775 and DE-A-19606167.

The support component of the catalyst system of the present invention can be any organic or inorganic, inert solid, in particular a porous support such as talc, inorganic oxides and finely divided polymer powder (e.g. highly porous polyolefins such as polyethylene and polypropylene whose particle size and pore volume are similar to those of silica).

Suitable inorganic oxides may be found among the oxides of elements of main groups II–VI of the Periodic Table and transition groups III–IV of the Periodic Table of the Elements. Examples of oxides preferred as supports include silicon dioxide, aluminum oxide and also mixed oxides of the elements calcium, aluminum, silicon, magnesium, titanium and corresponding oxide mixtures. Other inorganic oxides which can be used either alone or in combination with the abovementioned preferred oxidic supports are, for example, MgO, $ZrO_2$, $TiO_2$ or $B_2O_3$, to name only a few. The support materials used have a specific surface area in the range from 10 to 1000 $m^2/g$, a pore volume in the range from 0.1 to 5 ml/g and a mean particle size of from 1 to 500 $\mu m$. Preference is given to supports having a specific surface area in the range from 50 to 500 $\mu m$, a pore volume in the range from 0.5 to 3.5 ml/g and a mean particle size in the range from 5 to 350 $\mu m$. Particular preference is given to supports having a specific surface area in the range from 200 to 400 $m^2/g$, a pore volume in the range from 0.8 to 3.0 ml/g and a mean particle size of from 10 to 200 $\mu m$.

If the support material used naturally has a low moisture content or residual solvent content, dehydration or drying before use can be omitted. If this is not the case, as when using silica gel as support material, dehydration or drying is advisable. Thermal dehydration or drying of the support material can be carried out under reduced pressure with simultaneous blanketing with inert gas (e.g. nitrogen). The drying temperature is in the range from 100 to 1000° C., preferably from 200 to 800° C. The pressure is not critical in this case. The duration of the drying process can be from 1 to 24 hours. Shorter or longer drying times are possible, provided that establishment of equilibrium with the hydroxyl groups on the support surface can take place under the conditions chosen, which normally takes from 4 to 8 hours.

Dehydration or drying of the support material can also be carried out by chemical means, by reacting the adsorbed water and the hydroxyl groups on the surface with suitable passivating agents. Reaction with the passivating reagent can convert all or part of the hydroxyl groups into a form which does not lead to any adverse interaction with the catalytically active centers. Suitable passivating agents are, for example, silicon halides and silanes, e.g. silicon tetrachloride, chloride trimethylsilane, dimethylamino trichlorosilane, or organometallic compounds of aluminum, boron and magnesium, for example trimethylaluminum, triethylaluminum, triisobutylaluminum, triethylborane, dibutylmagnesium. Chemical dehydration or passivation of the support material is carried out, for example, by reacting a suspension of the support material in a suitable solvent with the passivating reagent either in pure form or as a solution in a suitable solvent in the absence of air and moisture. Suitable solvents are, for example, aliphatic or aromatic hydrocarbons such as pentane, hexane, heptane, toluene or xylene. Passivation is carried out at from 25° C. to 120° C., preferably from 50 to 70° C. Higher and lower temperatures are possible. The reaction time is from 30 minutes to 20 hours, preferably from 1 to 5 hours. After the chemical dehydration is complete, the support material is isolated by filtration under inert conditions, washed one or more times with suitable inert solvents as described above and subsequently dried in a stream of inert gas or under reduced pressure.

Organic support materials such as finely divided polyolefin powders (e.g. polyethylene, polypropylene or polystyrene) can also be used and should likewise be freed of adhering moisture, solvent residues or other impurities by appropriate purification and drying operations before use.

To prepare the supported catalyst system, at least one of the above-described transition metal compounds of the formula VII is brought into contact with at least one cocatalyst component in a suitable solvent, preferably giving a soluble reaction product, an adduct or a mixture.

The preparation obtained in this way is then mixed with the dehydrated or passivated support material, the solvent is removed and the resulting supported transition metal compound catalyst system is dried to ensure that all or most of the solvent is removed from the pores of the support material. The supported catalyst is obtained as a free-flowing powder. A process for preparing a free-flowing and, if desired, prepolymerized transition metal compound catalyst system comprises the following steps:

a) preparation of a transition metal compound/cocatalyst mixture in a suitable solvent or suspension medium, with the transition metal compound component having one of the above-described structures, b) application of the transition metal compound/cocatalyst mixture to a porous, preferably inorganic dehydrated support, c) removal of the major part of the solvent from the resulting mixture, d) isolation of the supported catalyst system, e) if desired, prepolymerization of the supported catalyst system obtained using one or more olefinic monomer(s) to give a prepolymerized supported catalyst system.

Preferred solvents for preparing the transition metal compound/cocatalyst mixture are hydrocarbons and hydrocarbon mixtures which are liquid at the reaction temperature chosen and in which the individual components preferably dissolve. However, solubility of the individual components is not a prerequisite as long as it is ensured that the reaction product of transition metal compound and cocatalyst component is soluble in the solvent chosen. Examples of suitable solvents include alkanes such as pentane, isopentane, hexane, heptane, octane and nonane; cycloalkanes such as cyclopentane and cyclohexane; and aromatics such as benzene, toluene, ethylbenzene and diethylbenzene. Very particular preference is given to toluene.

The amounts of aluminoxane and transition metal compound used in the preparation of the supported catalyst system can be varied over a wide range. Preference is given to a molar ratio of aluminum to transition metal in the transition metal compounds of from 10:1 to 1000:1, very particularly preferably from 50:1 to 500:1.

In the case of methylaluminoxane, preference is given to using 30% strength toluene solutions; however, the use of 10% strength solutions is also possible.

To carry out the preactivation, the organometallic compound in the form of a solid is dissolved in a solution of the aluminoxane in a suitable solvent. It is also possible to dissolve the transition metal compound separately in a suitable solvent and subsequently to combine this solution with the aluminoxane solution. Preference is given to using toluene.

The preactivation time is from 1 minute to 200 hours.

The preactivation can take place at room temperature (25° C.). The use of higher temperatures can sometimes shorten the time required for the preactivation and produce an additional increase in activity. In this case, a higher temperature means one in the range from 50 to 100° C.

The preactivated solution or the transition metal compound/cocatalyst mixture is subsequently combined with an inert support material, usually silica gel, which is present in the form of a dry powder or as a suspension in one of the abovementioned solvents. Preference is given to using the support material as powder. The order of addition is immaterial. The preactivated transition metal compound/cocatalyst solution or the transition metal compound/cocatalyst mixture can be added to the support material or else the support material can be introduced into the solution.

The volume of the preactivated solution or the transition metal compound/cocatalyst mixture can exceed 100% of the total pore volume of the support material used or else can be up to 100% of the total pore volume.

The temperature at which the preactivated solution or the transition metal compound/cocatalyst mixture is brought into contact with the support material can vary in a range from 0 to 100° C. However, lower or higher temperatures are also possible.

All or the major part of the solvent is subsequently removed from the supported catalyst system, with the mixture being able to be stirred and, if desired, also heated during this procedure. Preference is given to removing both the visible proportion of the solvent and the proportion in the pores of the support material. The removal of the solvent can be carried out in a conventional fashion with application of vacuum and/or flushing with inert gas. In the drying process, the mixture can be heated until the free solvent has been removed, which usually takes from 1 to 3 hours at a preferred temperature of from 30 to 60° C. The free solvent is the visible proportion of solvent in the mixture. In this context, residual solvent is the proportion which is enclosed in the pores. As an alternative to complete removal of the solvent, it is also possible for the supported catalyst system to be dried only to a particular residual solvent content, with the free solvent having been completely removed. The supported catalyst system can subsequently be washed with a low-boiling hydrocarbon such as pentane or hexane and dried again.

The supported catalyst system prepared according to the present invention can either be used directly for the polymerization of olefins or can be prepolymerized using one or more olefinic monomers prior to use in a polymerization process. The procedure for prepolymerizing supported catalyst systems is described, for example, in WO 94/28034.

A small amount of an olefin, preferably an α-olefin (for example vinyl cyclohexane, styrene or phenyldimethylvinylsilane) as modifying component or an antistatic (as described in U.S. Ser. No. 08/365,280) can be added as additive during or after the preparation of the supported catalyst system. The molar ratio of additive to organometallic compound I is preferably from 1:1000 to 1000:1, very particularly preferably from 1:20 to 20:1.

The present invention also provides a process for preparing a polyolefin by polymerization of one or more olefins in the presence of the novel catalyst system comprising at least one transition metal component of the formula I. For the purposes of the present invention, the term polymerization refers to both a homopolymerization and a copolymerization.

Preference is given to polymerizing olefins of the formula $R_m$—CH=CH—$R_n$, where $R_m$ and $R_n$ are identical or different and are a hydrogen atom or a carbon-containing radical having from 1 to 20 carbon atoms, in particular from 1 to 10 carbon atoms, and $R_m$ and $R_n$, together with the atoms connecting them, may form one or more rings.

Examples of such olefins are 1-olefins having 2–20 carbon atoms, preferably from 2 to 10 carbon atoms, e.g. ethene, propene, 1-butene, 1-pentene, 1-hexene, 4-methyl-1-pentene or 1-octene, styrene, dienes such as 1,3-butadiene, 1–4-hexadiene, vinylnorbornene, norbornadiene, ethylnorbornadiene and cyclic olefins such as norbornene, tetracyclododecene or methylnorbornene. In the process of the present invention, preference is given to homopolymerizing ethene or propene or copolymerizing propene with ethene and/or with one or more 1-olefins having from 4 to 20 carbon atoms, e.g. butene, hexene, styrene or vinylcyclohexane, and/or one or more dienes having from 4 to 20 carbon atoms, e.g. 1,4-butadiene, norbornadiene, ethylidenenorbornene or ethenenorbornadiene. Examples of such copolymers are ethene-propene copolymers, ethene-norbornene copolymers, ethene-styrene copolymers or ethene-propene-1,4-hexadiene terpolymers. The polymerization is carried out at from 0 to 300° C., preferably from 50 to 200° C., very particularly preferably 50–80° C. The pressure is from 0.5 to 2000 bar, preferably from 5 to 64 bar.

The polymerization can be carried out in solution, in bulk, in suspension or in the gas phase, continuously or batchwise, in one or more stages. The catalyst system prepared according to the present invention can be used as sole catalyst component for the polymerization of olefins having from 0.2 to 20 carbon atoms, or preferably in combination with at least one alkyl compound of elements of main groups I to III of the Periodic Table, e.g. an aluminum, magnesium or lithium alkyl or an aluminoxane. The alkyl compound is added to the monomer or suspension medium and serves to free the monomer of substances which can adversely affect the catalyst activity. The amount of alkyl compound added depends on the quality of the monomers used. If necessary, hydrogen is added as molar mass regulator and/or to increase the activity.

The catalyst system can be introduced into the polymerization system in pure form or can be admixed with inert components such as paraffins, oils or waxes to improve meterability. In addition, an antistatic can be introduced into the polymerization system either together with or separately from the catalyst system used.

The polymers prepared using the catalyst system of the present invention display a uniform particle morphology and contain no fines. No deposits or cake material are formed in the polymerization using the catalyst system of the present invention.

The copolymers obtained by use of the catalyst system of the present invention can be prepared with a high productivity at industrially relevant process parameters without deposit formation. The catalyst system thus makes it possible to prepare copolymers having a high comonomer content and a high molar mass.

The invention is illustrated by the following examples which do not, however, restrict the scope of the invention.

General information: preparation and handling of organometallic compounds were carried out in the absence of air and moisture under argon (Schlenk Technique or Glove Box). All solvents required were purged with argon and dried over molecular sieves before use.

The preparation of the imine starting materials is carried out by the methods described in the literature. Examples may be found, for example, in Chem. Rev. 1963, 63, 489–510. Some of them are chemicals which can be procured commercially.

Preparation of the Sodium and Lithium Salts

EXAMPLE 1

Preparation of N-isopropylsalicylaldiminatolithium 6 g (40.2 mmol) of isopropylsalicylaldimine are dissolved in 75 ml of toluene and admixed at 0° C. with 16.1 ml of a 2.5 molar solution of butyllithium. The mixture is subsequently warmed to room temperature and stirred at this temperature for 3 hours. During this time, a white precipitate is obtained and this is separated off by means of a G4 frit. The white precipitate is washed once with 5 ml of toluene and the residue is dried in an oil pump vacuum. This gives 4.41 g (65%) of the desired product.

EXAMPLE 2

Preparation of N-cyclohexylsalicylaldiminatolithium 8 g (39.4 mmol) of cyclohexylsalicylaldimine are dissolved in 100 ml of toluene and admixed at 0° C. with 24.6 ml of a 1.6 molar solution of butyllithium in hexane. The mixture is subsequently warmed to room temperature and stirred at this temperature for 3 hours. During this time, a white precipitate is obtained. The suspension is evaporated to half the volume of solvent and the precipitate is separated off by means of a G4 frit. The white precipitate is washed once with 5 ml of toluene and 5 ml of pentane and the residue is dried in an oil pump vacuum. This gives 5.18 g (70%) of the desired product.

EXAMPLE 3

Preparation of N-cyclohexylsalicylaldiminatosodium 8.1 g (39.8 mmol) of cyclohexylsalicylaldimine are dissolved in 60 ml of methanol and admixed at room temperature with 7.2 g (39.8 mmol) of sodium methoxide solution. The mixture is subsequently stirred overnight at room temperature. The solvent is subsequently removed on a rotary evaporator and the residue is stirred with 50 ml of pentane at this temperature. The yellow residue is isolated on a G4 frit and washed with 5 ml of pentane. The residue is then dried in an oil pump vacuum to give 6.04 g (68%) of the desired product.

EXAMPLE 4

Preparation of N-isopropylsalicylaldiminatosodium 6.8 g (45.6 mmol) of N-isopropylsalicylaldimine are dissolved in 40 ml of methanol and admixed at room temperature with 8.2 g (45.6 mmol) of sodium methoxide solution. The mixture is subsequently stirred overnight at room temperature. The solvent is subsequently removed on a rotary evaporator and the residue is stirred with 50 ml of pentane at this temperature. The yellow residue is isolated on a G4 frit and washed with 5 ml of pentane. The residue is then dried in an oil pump vacuum to give 5.8 g (69%) of the desired product.

EXAMPLE 5
Preparation of N-phenylsalicylaldiminatosodium 8 g (40.6 mmol) of N-phenylsalicylaldimine are dissolved in 85 ml of methanol and admixed at room temperature with 7.3 g (40.6 mmol) of sodium methoxide solution. The mixture is subsequently stirred overnight at room temperature. The solvent is subsequently removed on a rotary evaporator and the residue is stirred with 30 ml of pentane at this temperature. The yellow residue is isolated on a G4 frit and washed with 5 ml of pentane. The residue is then dried in an oil pump vacuum to give 8.5 g (96%) of the desired product.

EXAMPLE 6
Preparation of N-2,6-diisopropylphenylsalicylaldiminato Sodium 8 g (39.5 mmol) of N-2,6-diisopropylphenylsalicylaldimine are dissolved in 85 ml of methanol and admixed at room temperature with 7.1 g (40.6 mmol) of sodium methoxide solution. The mixture is subsequently stirred overnight at room temperature. The solvent is subsequently removed on a rotary evaporator and the residue is stirred with 30 ml of pentane at this temperature. The yellow residue is isolated on a G4 frit and washed with 5 ml of pentane. The residue is then dried in an oil pump vacuum to give 7.5 g (61%) of the desired product.

EXAMPLE 7
Preparation of N-2,6-diisopropyl-3,5-di-tert-butylsalicylaldiminatosodium 9 g (22.9 mmol) of N-2,6-diisopropyl-3,5-di-tert-butylsalicylaldimine are dissolved in 100 ml of methanol and admixed at room temperature with 4 g (22.9 mmol) of sodium methoxide solution. The mixture is subsequently stirred overnight at room temperature. The solvent is subsequently removed on a rotary evaporator and the residue is stirred with 30 ml of pentane at this temperature. The yellow residue is isolated on a G4 frit and washed with 5 ml of pentane. The residue is then dried in an oil pump vacuum to give 8.8 g (92%) of the desired product.

EXAMPLE 8
Preparation of N-cyclohexyl-3,5-di-tert-butylsalicylaldiminato Lithium 10 g (29.7 mmol) of N-cyclohexyl-3,5-di-tert-butylsalicylaldimine are dissolved in 100 ml of toluene and admixed at 0° C. with 19.7 mol of a 1.6 molar solution of butyllithium in hexane. The mixture is subsequently warmed to room temperature and stirred at this temperature for 5 hours. During this time, a white precipitate is formed. The suspension is evaporated to half the volume of solvent and the precipitate is separated off by means of a G4 frit. The white precipitate is washed once with 10 ml of toluene and 5 ml of pentane and the residue is dried in an oil pump vacuum. This gives 7.7 g (77%) of the desired product.

Preparation of Monosilylated Indenes

EXAMPLE 9
Preparation of 2-methyl-4-(4'-tert-butylphenyl)-1-dimethylchlorosilylindene 20.0 g (76 mmol) of 2-methyl-4-(4'-tert-butylphenyl) indene together with 160 ml of toluene and 5 ml of DME are placed in a reaction vessel. 28.4 ml (76 mmol) of a butyllithium solution are added dropwise to this solution, and the mixture is stirred at 80° C. for another 1 hour after the addition is complete. The reaction solution formed in this way is slowly added dropwise to a solution of 27.7 ml (229 mmol) of dimethyldichlorosilane in 260 ml of THF which has been precooled to −40° C. The reaction mixture is allowed to warm to room temperature and is stirred overnight. The solvent is subsequently removed in an oil pump vacuum and the residue which remains is taken up in 100 ml of toluene. The insoluble lithium chloride is separated off by means of a G4 frit and the solvent of the filtrate is removed in an oil pump vacuum. This gives 24.8 g (98%) of the desired product.

$^1$H-NMR (400 MHz, CDCl$_3$): 7.3–7.0 (m, 7H, arom-H), 6.7 (s, 1H, olefin-H-indene), 3.5 (s, 1H, H-indene), 2.1 (s, 3H, CH$_3$), 1.3 (s, 9H, tert-butyl), 0.3, 0.05 (each s, each 3H, CH$_3$—Si).

EXAMPLE 10
Preparation of 2-ethyl-4-(4'-tert-butylphenyl)-1-dimethylchlorosilylindene 20.0 g (72.4 mmol) of 2-ethyl-4-(4'-tert-butylphenyl) indene together with 153 ml of toluene and 4.8 ml of DME are placed in a reaction vessel. 27.0 ml (72.4 mmol) of a butyllithium solution are added dropwise to this solution, and the mixture is stirred at 80° C. for another 1 hour after the addition is complete. The reaction solution formed in this way is slowly added dropwise to a solution of 26.3 ml (217 mmol) of dimethyldichlorosilane in 248 ml of THF which has been precooled to −40° C. The reaction mixture is allowed to warm to room temperature and is stirred overnight. The solvent is subsequently removed in an oil pump vacuum and the residue which remains is taken up in 100 ml of toluene. The insoluble lithium chloride is separated off by means of a G4 frit and the solvent of the filtrate is removed in an oil pump vacuum. This gives 25.5 g (95%) of the desired product.

$^1$H-NMR (400 MHz, CDCl$_3$): 7.3–7.0 (m, 7H, arom-H), 6.7 (s, 1H, olefin-H-indene), 3.6 (s, 1H, H-indene), 2.6, 2.4 (each s, 1H, CH2), 1.3 (s, (H, tert-butyl, 1.1 (t, 3H, CH3), 0.3, 0.0 (each s, each 3H, CH$_3$—Si).

EXAMPLE 11
Preparation of 2-methyl(4-thiapentalene)-1-dimethylchlorosilane 20.0 g (14.8 mmol) of 2-methyl(2-hydrocyclopenta[2,1-b]thiophene) together with 260 ml of toluene and 8 ml of DME are placed in a reaction vessel. 55.3 ml (148 mmol) of a butyllithium solution are added dropwise to this solution, and the mixture is stirred at 80° C. for another 1 hour after the addition is complete. The reaction solution formed in this way is slowly added dropwise to a solution of 53.9 ml (446 mmol) of dimethyldichlorosilane in 460 ml of THF which has been precooled to −40° C. The reaction mixture is allowed to warm to room temperature and is stirred overnight. The solvent is subsequently removed in an oil pump vacuum and the residue which remains is taken up in 100 ml of toluene. The insoluble lithium chloride is separated off by means of a G4 frit and the solvent of the filtrate is removed in an oil pump vacuum. This gives 29.1 g (86%) of the desired product.

$^1$H-NMR (400 MHz, CD$_2$Cl$_2$): 7.3–6.8 (m, 2H), 6.7–6.4 (m, 1H), 4.0–3.4 (m, 2H), 2.6 (m, 3H, CH$_3$), 0.3–0.05 (each s, each 3H, CH$_3$—Si).

EXAMPLE 12
Preparation of 2-isopropyl-4-(1-naphthyl)-1-dimethylchlorosilylindene 18.5 g (65 mmol) of 2-isopropyl-4-(1-naphthyl)indene together with 150 ml of toluene and 4.8 ml of DME are placed in a reaction vessel. 24.2 ml (65 mmol) of a butyllithium solution are added dropwise to this solution, and the mixture is stirred at 80° C. for another 1 hour after the addition is complete. The reaction solution formed in this way is slowly added dropwise to a solution of 26.2 ml (216 mmol) of dimethyldichlorosilane in 250 ml of THF which has been precooled to −40° C. The reaction mixture is allowed to warm to room temperature and is stirred overnight. The solvent is subsequently removed in an oil pump vacuum and the residue which remains is taken up in 100 ml of toluene. The insoluble lithium chloride is separated off by means of a G4 frit and the solvent of the filtrate is removed in an oil pump vacuum. This gives 23.4 g (95%) of the desired product.

$^1$H-NMR (400 MHz, CDCl$_3$): 7.45–7.32 (m, 7H, arom-H), 6.26 (s, 1H, olefin-H-indene), 3.69 (s, 1H, H-indene), 3.41 (m, 1H, CH-isopropyl), 2.15 (s, 3H, CH$_3$), 1.1, 0.9 (each d, each 3H, CH$_3$-isopropyl), 0.46, 0.18 (each s, each 3H, CH$_3$—Si).

Other indenyl-dimethylchlorosilane and heteropentalene-dimethylchlorosilane systems can be synthesized by methods analogous to the examples described above.

Preparation of Ligand Systems

EXAMPLE 13
Preparation of 2-methyl-7-(4'-tert-butylphenyl)-1-indene-dimethylsilanyloxybenzylidene-2-{2,6-diisopropylphenyl}aldimine (V-13)

5 g (17.8 mmol) of N-2,6-diisopropylphenylsalicylaldimine together with 40 ml of methylene chloride are placed in a reaction vessel, N-ethyldiisopropylamine is then added and the mixture is subsequently stirred at room temperature for 20 minutes. 7.63 g (17.8 mmol) of 2-methyl-4-(4'-tert-butylphenyl)-1-dimethylchlorosilylindene dissolved in 40 ml of methylene chloride are subsequently added and the reaction solution is stirred at this temperature for 2 hours. The solvent is removed in an oil pump vacuum and the oily residue which remains is stirred with 80 ml of pentane. The pulverulent residue formed is filtered off on a G4 frit and washed with 2×50 ml of pentane. Drying in an oil pump vacuum gives 4.7 g (47%) of the desired compound.

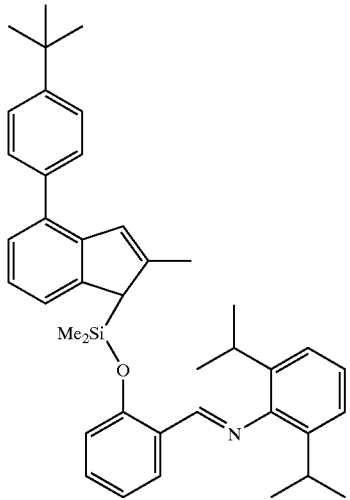

V-13

$^1$H-NMR (400 MHz, CDCl$_3$): 8.39 (s 1H, imine-H), 7.45–6.76 (m, 14H, arom-H), 6.33 (s, 1H, olefin-H-indene), 3.5 (s, 1H, H-indene), 3.12 (m, 2H, isopropyl-H), 1.71 (s, 3H, CH$_3$), 1.34 (s, 9-H, tert-butyl-H), 1.27 (dd, 12H, isopropyl-CH$_3$), 0.08 (s, 6H, CH$_3$—Si).

EXAMPLE 14
Preparation of 2-methyl-7-(4'-tert-butylphenyl)-1-indenedimethylsilanyloxybenzylidene-2-{phenyl}aldimine (V-14)

6 g (16.8 mmol) of 2-methyl-4-(4'-tert-butylphenyl)-1-dimethylchlorosilylindene are added to a suspension of 4.2 g (19.2 mmol) of N-phenylsalicylaldiminatosodium in 240 ml of THF. The mixture is stirred overnight. The sodium chloride formed is subsequently separated off by means of a G3 frit and the solvent of the filtrate is removed under an oil pump vacuum. This gives 6.0 g (69%) of an orange oil.

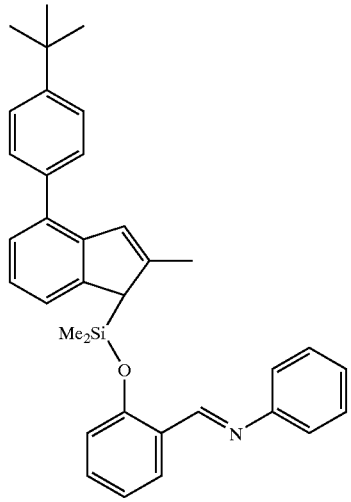

V-14

$^1$H-NMR (400 MHz, CDCl$_3$): 8.38 (s 1H, imine-H), 7.45–6.76 (m, 14H, arom-H), 6.30 (s, 1H olefin-H-indene), 3.47 (s, 1H, H-indene), 1.72 (s, 3H, CH$_3$), 1.34 (s, 9-H, tert-butyl-H), 0.09 (s, 6H, CH$_3$—Si).

EXAMPLE 15
Preparation of 2-methyl-7-(phenyl)-1-indenedimethylsilanyloxybenzylidene-2-{phenyl}aldimine (V-15)

10 g (33.5 mmol) of 2-methyl-4-(phenyl)-1-dimethylchlorosilylindene are added to a suspension of 7.3 g (19.2 mmol) of N-phenylsalicylylaldiminatosodium in 300 ml of THF. The mixture is stirred overnight. The sodium chloride formed is subsequently separated off by means of a G3 frit and the solvent of the filtrate is removed in an oil pump vacuum. This gives 8.0 g (52%) of a dark orange oil.

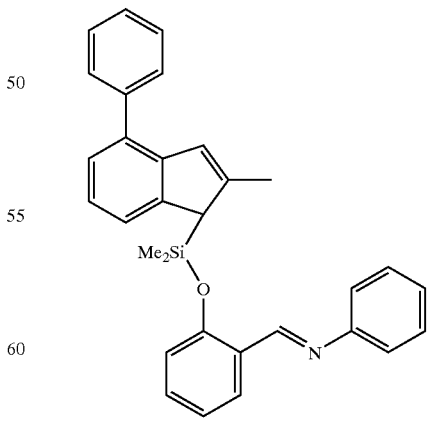

V-15

$^1$H-NMR (400 MHz, CDCl$_3$): 8.35 (s, 1H, imine-H), 7.49–6.76 (m, 14H, arom-H), 6.32 (s, 1H, olefin-H-indene), 3.51 (s, 1H, H-indene), 1.72 (s, 3H, CH$_3$), 0.10 (s, 6H, CH$_3$—Si).

EXAMPLE 16

Preparation of 2-methyl-7-(phenyl)-1-indenedimethylsilanyloxybenzylidene-2-{isopropyl}aldimine (V-16)

10 g (33.5 mmol) of 2-methyl-4-(phenyl)-1-dimethylchlorosilylindene dissolved in 70 ml of THF are added dropwise to a suspension of 5.7 g (33.5 mmol) of N-isopropylsalicylaldiminatolithium in 60 ml of toluene which has been precooled to −20° C. The reaction mixture is allowed to warm to room temperature and is stirred overnight. The solvent is subsequently removed in an oil pump vacuum and the residue is taken up in 100 ml of toluene. The lithium chloride formed is then separated off by means of a G3 frit and the solvent of the filtrate is removed in an oil pump vacuum. This gives 9.7 g (68%) of a dark orange oil.

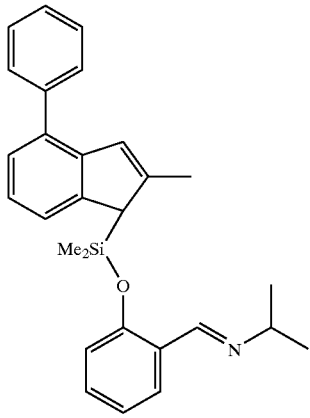

V-16

$^1$H-NMR (400 MHz, CDCl$_3$): 8.18 (s 1H, imine-H), 7.49–6.76 (m, 14H, arom-H), 6.35 (s, 1H, olefin-H-indene), 3.51 (s, 1H, H-indene), 3.47 (m, 1-H, isopropyl-H), 1.74 (s, 3H, CH$_3$), 1.23 (d, 6H, isopropyl-CH$_3$), 0.08 (s, 6H, CH$_3$—Si).

EXAMPLE 17

Preparation of 2-ethyl-7-(4'-tert-butylphenyl)-1-indenedimethylsilanyloxybenzylidene-2-{cyclohexyl}aldimine (V-17)

7.5 g (20.3 mmol) of 2-ethyl-4-(4'-tert-butylphenyl)-2-dimethylchlorosilylindene dissolved in 70 ml of THF are added dropwise to a solution of 4.2 g (20.3 mmol) of N-cyclohexylsalicylaldiminatolithium in 40 ml of toluene which has been precooled to −20° C. The reaction mixture is allowed to warm to room temperature and is stirred overnight. The solvent is subsequently removed in an oil pump vacuum and the residue is taken up in 100 ml of toluene. The lithium chloride formed is then separated off by means of a G3 frit and the solvent of the filtrate is removed in an oil pump vacuum. This gives 6.5 g (60%) of a dark orange oil.

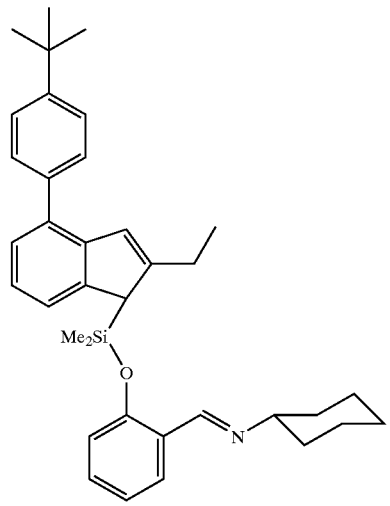

V-17

$^1$H-NMR (400 MHz, CDCl$_3$): 8.20 (s 1H, imine-H), 7.49–6.76 (m, 12H, arom-H), 6.35 (s, 1H, olefin-H-indene), 3.51 (s, 1H, H-indene), 3.08 (m, 1H, cyclohexyl-CH), 2.8, 2.6 (each m, 1H, CH$_2$), 1.69 (s, 3H, CH$_3$), 1.36 (s, 9-H, tert-butyl-H), 1.76, 1.44 (m, 10H, cyclohexyl-CH$_2$), 0.08 (s, 6H, CH$_3$—Si).

EXAMPLE 18

Preparation of 2-isopropyl-7-(naphthyl)-1-indenedimethylsilanyloxybenzylidene-2-{cyclohexyl}aldimine (V-18)

9.5 g (25.2 mmol) of 2-isopropyl-4-(naphthyl)-1-dimethylchlorosilylindene dissolved in 70 ml of THF are added dropwise to a suspension of 5.2 g (20.3 mmol) of N-cyclohexylsalicylaldiminatolithium in 60 ml of toluene which has been precooled to −20° C. The reaction mixture is allowed to warm to room temperature and is stirred overnight. The solvent is subsequently removed in an oil pump vacuum and the residue is taken up in 100 ml of toluene. The lithium chloride formed is then separated off by means of a G3 frit and the solvent of the filtrate is removed in an oil pump vacuum. This gives 8.5 g (62%) of a dark brown oil.

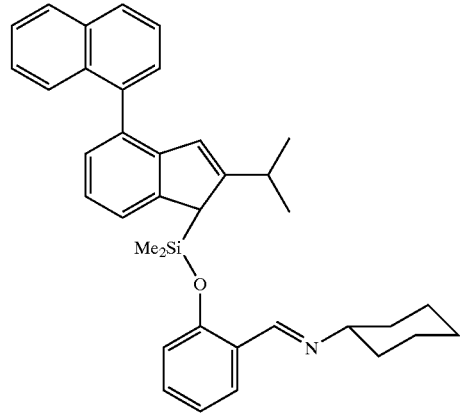

V-18

$^1$H-NMR (400 MHz, CDCl$_3$): 8.20 (s 1H, imine-H), 7.49–6.76 (m, 14H, arom-H), 6.35 (s, 1H, olefin-H-indene), 3.51 (s, 1H, H-indene), 3.47 (m, 1-H, isopropyl-H), 3.08 (m, 1H, cyclohexyl-CH), 1.1, 0.9 (each d, each 3H, CH$_3$-isopropyl), 1.76, 1.44 (m, 10H, cyclohexyl-CH$_2$), 0.08 (s, 6 h, CH$_3$—Si).

EXAMPLE 19

Preparation of 2-methyl-(4-thiapentalene)dimethylsilanyl-1-oxy-2,4-di-tert-butylbenzylidene{2,6-diisopropylphenyl}-aldimine (V-19)

6 g (26.2 mmol) of 2-methyl-(4-thiapentalene)-1-dimethylchlorosilane are added to a suspension of 10.9 g (26.2 mmol) of N-2,6-diisopropyl-3,5-di-tert-butylsalicylaldiminatosodium in 300 ml of THF. The mixture is stirred overnight. The sodium chloride formed is subsequently filtered off by means of a G3 frit and the solvent of the filtrate is removed in an oil pump vacuum. This gives 8.0 g (55%) of an orange oil.

V-19

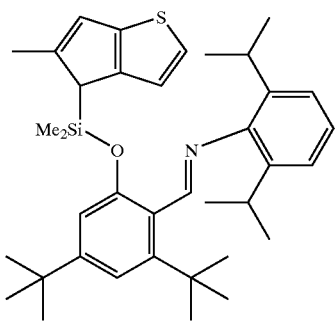

$^1$H-NMR (400 MHz, CDCl$_3$): 8.39 (s 1H, imine-H), 7.3–6.8 (m, 2H), 6.7–6.4 (m, 1H), 4.0–3.4 (m, 2H), 3.12 (m, 2H, isopropyl-H), 1.9 (m, 3H, CH$_3$), 1.34 (s, 9-H, tert-butyl-H), 1.27 (dd, 12H, isopropyl-CH$_3$), 0.3–0.05 (each s, each 3H, CH$_3$—Si).

Preparation of Complexes

EXAMPLE 20

Preparation of dimethylsilanyloxy(butylbenzylidene)-{N-2,6-diisopropylphenyl)aminato}(2-methyl-7-(4'-tert-butylphenyl)-1-indenyl)zirconium Dichloride (V-20)

11.12 g (17.8 mmol) of 2-methyl-7-(4-tert-butylphenyl)-1-indenedimethylsilanyl-1-oxyphenyl-2-{2,6-diisopropylphenyl}aldimine together with 60 ml of diethyl ether are placed in a reaction vessel and the mixture is cooled to 0° C. 14.2 ml of butyllithium (35.6 mmol) are subsequently added dropwise at such a rate that the temperature does not exceed 5° C. The reaction mixture is then allowed to warm to room temperature and is stirred overnight. The reaction solution is subsequently cooled to 0° C. and 4.2 g (18 mmol) of zirconium tetrachloride are added a little at a time. The mixture is allowed to warm to room temperature and is stirred for another 2 hours. The solvent is then removed in an oil pump vacuum and the oily residue which remains is taken up in 80 ml of toluene. The insoluble lithium chloride is separated off by means of a G4 frit. The solvent is removed from the filtrate, and the residue is stirred with 50 ml of pentane. The yellow pulverulent residue formed is filtered off by means of a G4 frit and washed with 2×50 ml of pentane. Drying in an oil pump vacuum gives 8.5 g (58%) of the desired compound.

V-20

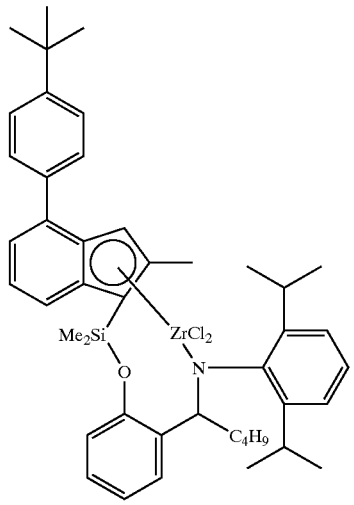

$^1$H-NMR (400 MHz, CDCl$_3$): 7.40–6.76 (m, 14H, arom-H), 6.39 (s, 1H, olefin-H-indene), 3.9 (dd, 1H, CH), 3.4 (m, 2H, isopropyl-H), 1.75 (s, 3H, CH$_3$), 1.70, 1.33, 1.29 (each m, each 2H, CH$_2$), 1.34 (s, 9-H, tert-butyl-H), 1.29 (dd, 12H, isopropyl-CH$_3$), 1.08, 1.01 (each s, each 3H, CH$_3$—Si), 0.96 (m, 3H, CH$_3$).

EXAMPLE 21

Preparation of dimethylsilanyloxy(butylbenzylidene)-{(N-phenyl)aminato}(2-methyl-7-(4'-tert-butylphenyl)-1-indenyl)zirconium Dichloride (V-21)

6.45 g (12.6 mmol) of 2-methyl-7-(4'-tert-butylphenyl)-1-indenedimethylsilanyl-1-oxyphenyl-2-{N-phenyl}aldimine together with 66 ml of diethyl ether are placed in a reaction vessel and the mixture is cooled to −78° C. 9.9 ml of butyllithium (25.2 mmol) are subsequently added dropwise at such a rate that the temperature does not exceed −60° C. The reaction mixture is then allowed to warm to room temperature and is stirred overnight. The reaction solution is subsequently cooled to 0° C. and 3.0 g (12.6 mmol) of zirconium tetrachloride are added a little at a time. The mixture is allowed to warm to room temperature and is stirred for another 2 hours. The solvent is then removed in an oil pump vacuum and the oily residue which remains is taken up in 60 ml of toluene. The insoluble lithium chloride is separated off by means of a G4 frit. The solvent is removed from the filtrate, and the residue is stirred with 40 ml of pentane. The yellow pulverulent residue formed is filtered off by means of a G4 frit and washed with 2×50 ml of pentane. Drying in an oil pump vacuum gives 6.5 g (70%) of the desired compound.

V-21

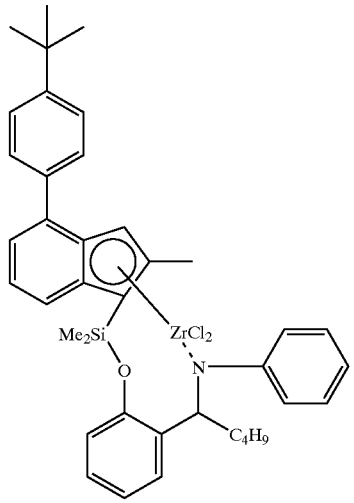

$^1$H-NMR (400 MHz, CDCl$_3$): 7.45–6.76 (m, 14H, arom-H), 6.39 (s, 1H, olefin-H-indene), 3.7 (dd, 1H, CH), 1.75 (s, 3H, CH$_3$), 1.65, 1.29, 1.27 (each m, each 2H, CH$_2$), 1.34 (s, 9-H, tert-butyl-H), 1.06, 1.04 (each s, each 3H, CH$_3$—Si), 0.92 (m, 3H, CH$_3$).

EXAMPLE 22
Preparation of dimethylsilanyloxy(butylbenzylidene)-{(N-phenyl)aminato}(2-methyl-7-(phenyl)-1-indenyl)titanium Dichloride (V-22)

5 g (10.8 mmol) of 2-methyl-7-(phenyl)-1-indenedimethylsilanyl-1-oxyphenyl-2-{N-phenyl}-aldimine together with 40 ml of diethyl ether are placed in a reaction vessel and the mixture is cooled to −78° C. 8.54 ml of butyllithium (21.6 mmol) are subsequently added dropwise at such a rate that the temperature does not exceed −60° C. The reaction mixture is then allowed to warm to room temperature and is stirred overnight. The reaction solution is subsequently cooled to 0° C. and 2.05 g (10.8 mmol) of titanium tetrachloride are added a little at a time. The mixture is allowed to warm to room temperature and stirred for another 2 hours. The insoluble lithium chloride is separated off by means of a G4 frit. The solvent is removed from the filtrate, the residue is stirred with 40 ml of pentane. The dark orange pulverulent residue formed is filtered off on a G4 frit and washed with 2×30 ml of pentane. Drying in an oil pump vacuum gives 4.3 g (59%) of the desired compound.

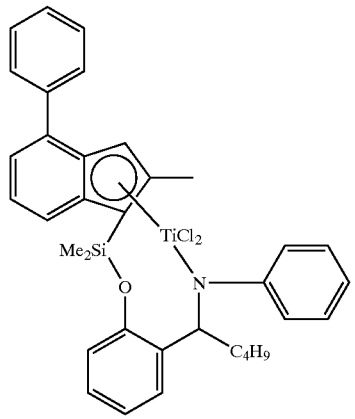

V-22

$^1$H-NMR (400 MHz, CDCl$_3$): 7.50–6.70 (m, 17H, arom-H), 6.37 (s, 1H, olefin-H-indene), 3.84 (dd, 1H, CH), 1.72 (s, 3H, CH$_3$), 1.81, 1.33, 1.27 (each m, each 2H, CH$_2$), 1.11, 1.09 (each s, each 3H, CH$_3$Si), 0.96 (m, 3H, CH$_3$).

EXAMPLE 23
Preparation of dimethylsilanyloxy(butylbenzylidene){(N-isopropyl)aminato}-(2-methyl-4-(phenyl)-1-indenyl)zirconium Dichloride (V-23)

7 g (16.4 mmol) of 2-methyl-7-(phenyl)-1-indenedimethylsilanyl-1-oxyphenyl-2{N-isopropyl}aldimine together with 40 ml of THF are placed in a reaction vessel and the mixture is cooled to −78° C. 12.9 ml of butyllithium (32.8 mmol) are subsequently added dropwise at such a rate that the temperature does not exceed −60° C. The reaction mixture is then allowed to warm to room temperature and is stirred for another 5 hours. The reaction solution is subsequently cooled to 0° C. and 5.42 g (10.8 mmol) of zirconium tetrachloride are added a little at a time. The mixture is allowed to warm to room temperature and stirred for another 2 hours. The insoluble lithium chloride is separated off by means of a G4 frit. The solvent is removed from the filtrate, and the residue is stirred with 50 ml of heptane. The dark yellow pulverulent residue formed is filtered off a G4 frit and washed with 2×30 ml of heptane. Drying in an oil pump vacuum gives 5.2 g (49%) of the desired compound.

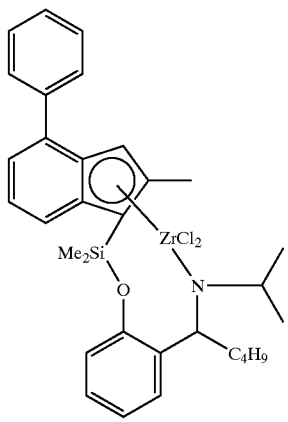

V-23

$^1$H-NMR (400 MHz, CDCl$_3$): 7.49–6.70 (m, 12H, arom-H), 6.35 (s, 1H, olefin-H-indene), 3.84 (dd, 1H, CH), 2.97 (m, 1-H, isopropyl-H), 1.72 (s, 3H, CH$_3$), 1.81, 1.33, 1.27 (each m, each 2H, CH$_2$), 1.05 (d, 6H, isopropyl-CH$_3$), 1.11, 1.09 (each s, each 3H, CH$_3$Si), 0.98 (m, 3H, CH$_3$).

EXAMPLE 24
Preparation of dimethylsilanyloxy(butylbenzylidene){(N-cyclohexyl)aminato}-(2-ethyl-4-(4'-tert-butylphenyl)-1-indenyl)zirconium Dichloride (V-24)

9 g (15.1 mmol) of 2-ethyl-4-(4'-tert-butylphenyl)-1-indenedimethylsilanyl-1-oxyphenyl-2{cyclohexyl}aldimine together with 50 ml of a mixture of THF/toluene (5:1) are placed in a reaction vessel and the mixture is cooled to −78° C. 11.8 ml of butyllithium (30.2 mmol) are subsequently added dropwise at such a rate that the temperature does not exceed −40° C. The reaction mixture is then allowed to warm to room temperature and is stirred for another 7 hours. The reaction solution is subsequently cooled to 0° C. and 3.52 g (15.1 mmol) of zirconium tetrachloride are added a little at a time. The mixture is allowed to warm to room temperature and is stirred for another 4 hours. The insoluble lithium chloride is separated off by means of a G4 frit. The solvent is removed from the filtrate, and the residue is stirred with 50 ml of heptane. The orange-yellow pulverulent residue formed is filtered off on a G4 frit and washed with 2×30 ml of heptane. Drying in an oil pump vacuum gives 5.2 g (49%) of the desired compound.

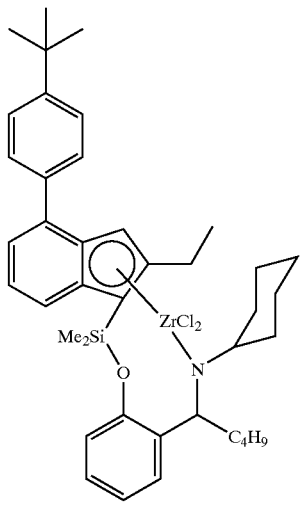

V-24

¹H-NMR (400 MHz, CDCl₃): 7.51–6.78 (m, 12H, arom-H), 6.32 (s, 1H, olefin-H-indene), 3.47 (m, 1-H, isopropyl-H), 3.08 (m, 1H, cyclohexyl-CH), 2.5, 2.1 (each m, each 1H, CH₂), 1.69 (each s, each 3H, CH₃), 1.36 (s, 9-H, tert-butyl-H), 1.79, 1.76, 1.42, 1.33, 1.27 (each m, each 2H, CH₂; due to coincidence of cyclohexyl and butyl radicals, an unambiguous assignment was not undertaken), 1.07, 1.02, (s, 6H, CH₃—Si).

EXAMPLE 25
Preparation of dimethylsilanyloxy(butylbenzylidene){N-cyclohexyl)aminato}-2-isopropyl-4-(naphthyl)-1-indenyl) zirconium Dichloride (v-25)

4 g (6.66 mmol) of 2-isopropyl-4-(naphthyl)-1-indenedimethylsilanyl-1-oxyphenyl-2-N-cyclohexyl) aldimine together with 30 ml of a mixture of THF/toluene (6:1) are placed in a reaction vessel and the mixture is cooled to −40° C. 5.2 ml of butyllithium (13.3 mmol) are subsequently added dropwise at such a rate that the temperature does not exceed −20° C. The reaction mixture is then allowed to warm to room temperature and is stirred for another 4 hours. The reaction solution is subsequently cooled to 0° C. and 1.55 g (15.1 mmol) of zirconium tetrachloride are added a little at a time. The mixture is allowed to warm to room temperature and stirred for another 4 hours. The insoluble lithium chloride is separated off by means of a G4 frit. The solvent is removed from the filtrate, and the residue is stirred with 50 ml of heptane. The orange-yellow pulverulent residue formed is filtered off on a G4 frit and washed with 2×30 ml of heptane. Drying in an oil pump vacuum gives 2.8 g (55%) of the desired compound.

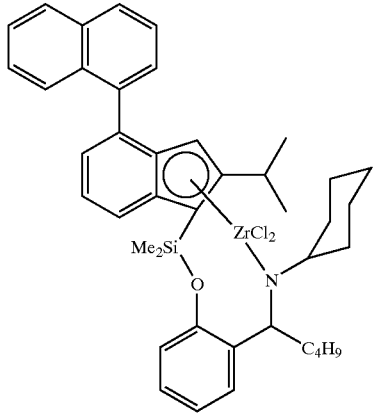

V-25

¹H-NMR (400 MHz, CDCl₃): 7.41–6.72 (m, 12H, arom-H), 6.37 (s, 1H, olefin-H-indene), 3.47 (m, 1-H, isopropyl-H), 3.57 (m, 1-H, isopropyl-H), 3.08 (m, 1H, cyclohexyl-CH), 2.5, 2.1 (each m, 1H, CH₂), 1.69 (each m, 3H, CH₃), 1.36 (s, 9-H, tert-butyl-H), 1.79, 1.76, 1.42, 1.33, 1.27 (each m, each 2H, CH₂; due to coincidence of cyclohexyl and butyl radicals, an unambiguous assignment was not undertaken), 1.1, 0.9 (each d, each 3H, CH₃-isopropyl), 1.11, 1.09 (s, 6H, CH₃—Si).

EXAMPLE 26
Preparation of Dimethylsilanyloxy(3,5-di-tert-butyl-butylbenzylidene){(N-2,6-diisopropylphenyl)aminato}(2-methyl-(4-thiapentalene)zirconium Dichloride (V-26)

8.5 g (16.0 mmol) of 2-methyl-(4-thiapentalene) dimethylsilanyl-1-oxy-3,5-di-tert-butylphenyl-2-{N-2,6-diisopropylphenyl}aldimine together with 60 ml of diethyl ether are placed in a reaction vessel and the mixture is cooled to 0° C. 12.8 ml of butyllithium (32.0 mmol) are subsequently added dropwise at such a rate that the temperature does not exceed 10° C. The reaction mixture is then allowed to warm to room temperature and is stirred overnight. The reaction solution is subsequently cooled to 0° C. and 3.72 g (18 mmol) of zirconium tetrachloride are added a little at a time. The mixture is allowed to warm to room temperature and stirred for another 2 hours. The solvent is then removed in an oil pump vacuum and the oily residue which remains is taken up in 80 ml of toluene. The insoluble lithium chloride is separated off by means of a G4 frit. The solvent is removed from the filtrate, and the residue is stirred with 40 ml of pentane. The yellow pulverulent residue formed is filtered off on a G4 frit and washed with 2×40 ml of pentane. Drying in an oil pump vacuum gives 3.7 g (33%) of the desired compound.

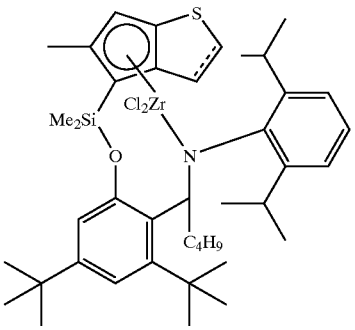

V-26

¹H-NMR (400 MHz, CDCl₃): 7.3–6.8 (m, 4H), 6.7–6.4 (m, 1H), 4.0–3.4 (m, 2H, isopropyl-H), 1.9 (m, 3H, CH₃), 1.34, 1.32 (each s, each 9-H, tert-butyl-H), 1.29, (dd, 12H, isopropyl-CH₃), 1.03, 0.99 (each s, each 3H, CH₃—Si).

EXAMPLE 27

Preparation of dimethylsilanyloxy(butylbenzylidene){N-cyclohexyl)aminato}-(2-ethyl-7-(4'-tert-butylphenyl)-1-indenyl)hafnium Dichloride (V-27)

10 g (16.8 mmol) of 2-ethyl-4-(4'-tert-butylphenyl)-1-indenedimethylsilanyl-1-oxyphenyl-2-{N-cyclohexyl}aldimine together with 60 ml of a mixture of THF/toluene (5:1) are placed in a reaction vessel and the mixture is cooled to −78° C. 13.1 ml of butyllithium (30.2 mmol) are subsequently added dropwise at such a rate that the temperature does not exceed −40° C. The reaction mixture is subsequently allowed to warm to room temperature and is stirred for another 7 hours. The reaction solution is subsequently cooled to 0° C. and 5.38 g (16.8 mmol) of zirconium tetrachloride are added a little at a time. The mixture is allowed to warm to room temperature and stirred for another 7 hours. The insoluble lithium chloride is separated off by means of a G4 frit. The solvent is removed from the filtrate, and the residue is stirred with 50 ml of heptane. The orange pulverulent residue formed is filtered off on a G4 frit and washed with 2×40 ml of heptane. Drying in an oil pump vacuum gives 7.2 g (43%) of the desired compound.

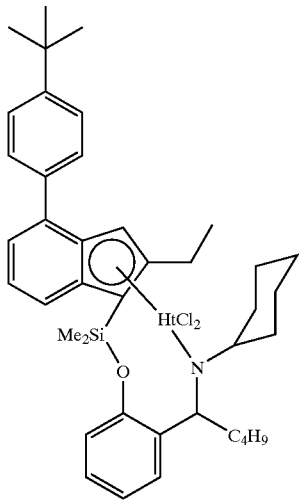

V-27

¹H-NMR (400 MHz, CDCl₃): 7.61–6.78 (m, 12H, arom-H), 6.35 (s, 1H, olefin-H-indene), 3.51 (m, 1-H, isopropyl-H), 3.10 (m, 1-H, cyclohexyl-CH), 2.7, 2.3 (each m, 1H, CH₂), 1.71 (s, 3H, CH₃), 1.34 (s, 9-H, tert-butyl-H), 1.80, 1.77, 1.44, 1.35, 1.28 (each m, each 2H, CH₂; due to coincidence of cyclohexyl and butyl radicals, an unambiguous assignment was not undertaken), 1.05, 1.01 (s, 6H, CH₃—Si).

Examples for the Synthesis According to Scheme 4

EXAMPLE 28

Preparation of 2-methyl-7-(4'-tert-butylphenyl)-1-indenedimethylsilanyloxy-benzaldehyde 1.78 ml (16.9 mmol) of salicylaldehyde together with 60 ml of toluene are placed in a reaction vessel, triethylamine is added and the mixture is subsequently stirred at room temperature for 30 minutes. 6 g (16.9 mmol) of 2-methyl-4-(4'-tert-butylphenyl)-1-dimethylchlorosilylindene dissolved in 60 ml of toluene are subsequently added and the reaction solution is stirred for 2 hours at this temperature. The solvent is removed in an oil pump vacuum and the oily residue which remains is washed with 2×50 ml of pentane. Drying in an oil pump vacuum gives 6.9 g (93%) of the desired compound.

EXAMPLE 29

Preparation of 2-methyl-7-(4'-tert-butylphenyl) indenedimethylsilanyloxybenzylidene-2-{isopropyl}aldimine (V-29)

6.96 g (8.53 mmol) of 2-methyl-7-(4'-tert-butylphenyl)-1-indenedimethylsilanyl-oxybenzaldehyde dissolved in 17 ml of toluene and 4.1 g of sodium sulfate are placed in a reaction vessel at room temperature, forming a suspension. 0.73 ml (29 mmol) of N-isopropylamine in 6.2 ml of toluene is subsequently added dropwise. The mixture is stirred overnight at room temperature. The sodium sulfate is removed by means of a G3 frit and the solvent of the filtrate is removed in an oil pump vacuum. This gives 7.39 g (97%) of a dark orange oil.

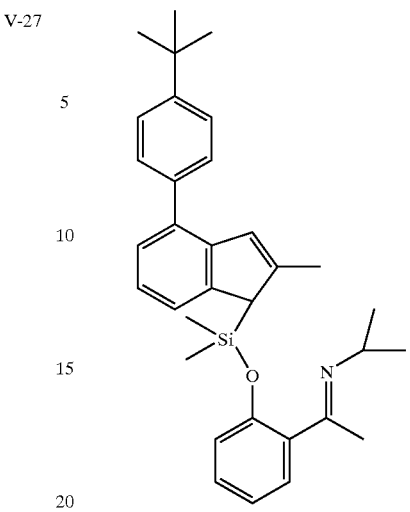

V-29

¹H-NMR (400 MHz, CDCl₃): 8.18 (s, 1H, imine-H), 7.49–6.76 (m, 14H, arom-H), 6.35 (s, 1H, olefin-H-indene), 3.51 (s, 1H, H-indene), 3.47 (m, 1-H, isopropyl-H), 1.74 (s, 3H, CH3), 1.36 (s, 9H, tert-butyl), 1.23 (d, 6H, isopropyl-CH3), 0.06 (s, 6H, CH₃—Si₃).

EXAMPLE 30

Preparation of Dimethylsilanyloxy(butylbenzylidene){N-isopropyl)aminato}(2-methyl-4-(4'-tert-butylphenyl)-1-indenyl)zirconium Dichloride (V-30)

3.3 (6.85 g mmol) of 2-methyl-7-(4'-tert-butylphenyl) indenedimethylsilanyloxybenzylidene-2-{isopropyl}aldimine together with 33 ml of diethylether are placed in a reaction vessel and the mixture is cooled to −78° C. 5.5 ml of butyllithium (13.7 mmol) are subsequently added dropwise at such a rate that the temperature does not exceed −60° C. The reaction mixture is then allowed to warm to room temperature and is stirred for another 2 hours. The reaction solution is subsequently cooled to 0° C. and 1.6 g (6.85 mmol) of zirconium tetrachloride is added a little at a time. The mixture is allowed to warm to room temperature and stirred for another 2 hours. The insoluble lithium chloride is separated off by means of a G4 frit. The solvent is removed from the filtrate, and the residue is stirred with 50 ml of heptane. The dark yellow pulverulent residue formed is filtered off on a G4 frit and washed with 2×30 ml of heptane. Drying in an oil pump vacuum gives 1.5 g (31%) of the desired compound.

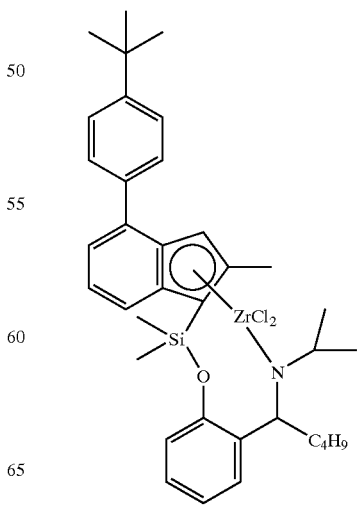

V-30

$^1$H-NMR (400 MHz, CDCl$_3$): 7.49–6.70 (m, 12H, arom-H), 6.35 (s, 1H, olefin-H-indene), 3.84 (dd, 1H, CH), 2.97 m, 1-H, isopropyl-H), 1.72 (s, 3H, CH$_3$), 1.81, 1.33, 1.27 (each m, each 2H, CH$_2$), 1.38 s, 9H, tert-butyl), 1.05 (d, 6H, isopropyl-CH$_3$), 1.11, 1.09 (each s, each 3H, CH$_3$—Si), 0.98 (m, 3H, CH$_3$).

Polymerization Results

General Preparation of the Catalyst System

80 μmol of the complexes described are dissolved at room temperature in 4.3 cm$^3$ (2D mmol of Al) of 30% strength methylaluminoxane solution in toluene. The solution is diluted with 3.7 cm$^3$ of toluene and stirred at room temperature for 1 hour. This reaction solution is subsequently added a little at a time to 4 g of SiO$_2$ (MS 948, from Grace, dried at 600° C. in a stream of argon) while stirring and the mixture is stirred for another 10 minutes after the addition is complete. The solvent is then removed in an oil pump vacuum until constant weight has been achieved. This results in pale pink free-flowing powders.

General Description of the Polymerization

Polymerization

For introduction into the polymerization system, 1 g of the supported catalyst system is resuspended in 20 cm$^3$ of Exxol.

In parallel thereto, a dry 16 dm$^3$ reactor is flushed firstly with nitrogen and subsequently with propylene and charged with 10 dm$^3$ of liquid propene. 8 cm$^3$ of a 20% strength triethylaluminum solution in Varsol are added as scavenger and the mixture is stirred at 30° C. for 15 minutes. The catalyst suspension was subsequently introduced into the reactor. The reaction mixture was heated to the polymerization temperature of 65° C. (4° C./min) and the polymerization system was maintained at 65° C. by means of cooling for 1 hour. The polymerization was stopped by venting the remaining propylene. The polymer was dried in a vacuum drying oven.

Polymerization Results

| Example | V-20 | V-21 | V-22 | V-23 | V-24 | V-25 | V-26 | V-27 | V-30 |
|---|---|---|---|---|---|---|---|---|---|
| Metallocene (mg)/g of cat. | 9.0 | 9.5 | 9.5 | 9.8 | 10.3 | 11.0 | 9.9 | 10.2 | 10.1 |
| PP (g) | 770* | 690* | 585* | 560* | 890* | 540* | 480* | 990* | 790* |
| Activity$^{1)}$ | 86 | 73 | 62 | 57 | 86 | 49 | 49 | 97 | 78 |
| M$_w$/M$_n$ | 2.2 | 2.3 | 2.2 | 2.4 | 2.4 | 2.5 | 2.2 | 2.3 | 2.3 |

$^{1)}$Activity: kg (polymer)/g of non-metallocene · h · bar
$^{2)}$*no deposit formation in the vessel, free-flowing polymer powder

We claim:

1. A compound of the formula (I):

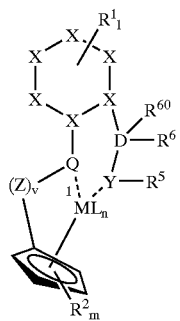

(I)

wherein

M$^1$ is a metal of transition group III, IV, V or VI of the Periodic Table of the Elements, R$^1$ are identical or different and are each a hydrogen atom or Si(R$^{12}$)$_3$, wherein R$^{12}$ are identical or different and are each a hydrogen atom or a C$_1$–C$_{40}$ group, or R$^1$ are identical or different and are each a C$_1$–C$_{30}$ group which is optionally fluorinated, or two or more radicals R$^1$ are joined to one another so that the radicals R$^1$ and the atoms of the cyclopentadienyl ring which connect them form a C$_4$–C$_{24}$ ring system which is optionally substituted, R$^2$ are identical or different and are each a hydrogen atom or Si(R$^{12}$)$_3$, wherein R$^{12}$ is as defined above, or R$^2$ are identical or different and are each a C$_1$–C$_{30}$ group which is optionally fluorinated C$_5$–C$_{24}$-heteroaryl which together with the cyclopentadienyl ring form azapentalenes, thiapentalenes or phosphapentalenes, or two or more radicals R$^2$ are joined to one another so that the radicals R$^2$ and the atoms of the cyclopentadienyl ring which connect them form a C$_4$–C$_{24}$ ring system which is optionally substituted, R$^5$ and R$^6$ are identical or different and are each a hydrogen atom or Si(R$^{12}$)$_3$, wherein R$^{12}$ is as defined above, or R$^5$ and R$^6$ are identical or different and are each a C$_1$–C$_{30}$ group which is optionally fluorinated, or the radicals R$^5$ and R$^6$ are joined to one another so that the radicals R$^5$ and R$^6$ form a C$_4$–C$_{24}$ ring system which is optionally substituted, R$^{60}$ is a hydrogen atom or a C$_1$–C$_{12}$-alkyl group, l is 5 when v=0 and l is 4 when v–1, m is 5 when v=0 and m is 4 when v=1, D, Q and Y independently are each an element of main group III, IV, V or VI of the Periodic Table of the Elements, X are identical or different and are each an element of main group III, IV, V or VI of the Periodic Table of the Elements and optionally form cyclic systems, L are identical or different and are each a hydrogen atom, a C$_1$–C$_{10}$-hydrocarbon group, a halogen atom or OR$^9$, SR$^9$, OSiR$_3^9$, SiR$_3^9$, PR$_2^9$ or NR$_2^9$, wherein R$^9$ is a halogen atom, a C$_1$–C$_{10}$-alkyl group, a halogenated C$_1$–C$_{10}$-alkyl group, a C$_6$–C$_{20}$-aryl group or a halogenated C$_6$–C$_{20}$-aryl group, or L is a toluenesulfonyl, trifluoroacetyl, trifluoroacetoxyl, trifluoromethanesulfonyl, nonafluorobutanesulfonyl or 2,2,2-trifluoroethanesulfonyl group, n is an integer from 1 to 4, Z is a bridging structural element and v is 0 or 1.

2. The compound as claimed in claim 1, wherein
$R^1$ are identical or different and each are a hydrogen atom, $Si(R^{12})_3$ wherein $R^{12}$ are identical or different and are each a hydrogen atom, $C_1–C_{20}$-alkyl, $C_1–C_{10}$-fluoroalkyl, $C_1–C_{10}$-alkoxy, $C_6–C_{20}$-aryl, $C_6–C_{10}$-fluoroaryl, $C_6–C_{10}$-aryloxy, $C_2–C_{10}$-alkenyl, $C_7–C_{40}$-arylalkyl, $C_7–C_{40}$-alkylaryl or $C_8–C_{40}$-arylalkenyl, or
$R^1$ are identical or different and are each a $C_1–C_{25}$-alkyl, $C_2–C_{25}$-alkenyl, $C_3–C_{15}$-alkylalkenyl, $C_6–C_{24}$-aryl, $C_5–C_{24}$-heteroaryl, $C_7–C_{30}$-arylalkyl, $C_7–C_{30}$-alkylaryl, fluorinated $C_1–C_{25}$-alkyl, fluorinated $C_6–C_{24}$-aryl, fluorinated $C_7–C_{30}$-arylalkyl, fluorinated $C_7–C_{30}$-alkylaryl or $C_1–C_{12}$-alkoxy,
or two or more radicals $R^1$ may be joined to one another so that the radicals $R^1$ and the atoms of the cyclopentadienyl ring which connect them form a $C_4–C_{24}$ ring system which is optionally substituted,
$R^5$ and $R^6$ are identical or different and are each a hydrogen atom or $Si(R^{12})_3$, wherein $R^{12}$ is defined above or $R^5$ and $R^6$ are identical or different and each are a $C_1–C_{25}$-alkyl, $C_2–C_{25}$-alkenyl, $C_3–C_{15}$-alkylalkenyl, $C_6–C_{24}$-aryl, $C_5–C_{24}$-heteroaryl, $C_7–C_{30}$-arylalkyl, $C_7–C_{30}$alkylaryl, fluorinated $C_1–C_{25}$-alkyl, fluorinated $C_6–C_{24}$-aryl, fluorinated $C_7–C_{30}$-arylalkyl, fluorinated $C_7–C_{30}$-alkylaryl or $C_1–C_{12}$-alkoxy,
or the radicals $R^5$ and $R^6$ are joined to one another so that the radicals $R^5$ and $R^6$ form a $C_4–C_{24}$ ring system which is optionally substituted,
X are identical or different and are each an element of the main group III, IV, V or VI of the Periodic Table of Elements and optionally form aromatic systems or cyclic systems of aliphatics with each other,
L are identical or different and are each a hydrogen atom, a $C_1–C_{10}$-alkyl or $C_6–C_{10}$-aryl a halogen atom, $OR^9$, $SR^9$, $OSiR^9_3$, $SiR^9_3$, $PR^9_2$ or $NR^9_2$ wherein $R^9$ is a halogen atom, a $C_1–C_{10}$-alkyl group, a halogenated $C_1–C_{10}$-alkyl group, a $C_6–C_{20}$-aryl group or a halogenated $C_6–C_{20}$-aryl group, or L is a toluenesulfonyl, trifluoroacetyl, trifluoroacetoxyl, trifluoromethanesulfonyl, nonafluorobutanesulfonyl or 2,2,2-trifluoroethanesulfonyl group.

3. The compound as claimed in claim 1, wherein
$M^1$ is Ti, Zr, Hf, Ni, Co, Fe, Pd, Sc, Cr and Nb
$R^1$ are identical or different and are each a hydrogen atom or $Si(R^{12})_3$, where $R^{12}$ are identical or different and are each a hydrogen atom, $C_1–C_{20}$-alkyl, $C_1–C_{10}$-fluoroalkyl, $C_1–C_{10}$-alkoxy, $C_6–C_{20}$-aryl, $C_6–C_{10}$-fluoroaryl, $C_6–C_{10}$-aryloxy, $C_2–C_{10}$-alkenyl, $C_7–C_{40}$-arylalkyl, $C_7–C_{40}$-alkylaryl or $C_8–C_{40}$-arylalkeny,
or $R^1$ are identical of different and are each $C_1–C_{25}$-alkyl, $C_2–C_{25}$-alkenyl, $C_3–C_{15}$-alkylalkenyl, $C_6–C_{24}$-aryl, $C_5–C_{24}$-heteroaryl, $C_7–C_{30}$-alkylaryl, $C_7–C_{30}$-alkylaryl, fluorinated $C_1–C_{25}$-alkyl, fluorinated $C_6–C_{24}$-aryl, fluorinated $C_7–C_{30}$-arylalkyl, fluorinated $C_7–C_{30}$-alkylaryl or $C_1–C_{12}$-alkoxy,
or two or more radicals $R^1$ are joined to one another so that the radicals $R^1$ and the atoms of the cyclopentadienyl ring which connect them form a $C_4–C_{24}$ ring system which is optionally substituted,
$R^2$ are identical or different and are each a hydrogen atom or $Si(R^{12})_3$, where $R^{12}$ are identical or different and are each a hydrogen atom, $C_1–C_{20}$-alkyl, $C_1–C_{10}$-fluoroalkyl, $C_1–C_{10}$-alkoxy, $C_6–C_{14}$-aryl, $C_6–C_{10}$-fluoroaryl, $C_6–C_{10}$-aryloxy, $C_2–C_{10}$-alkenyl, $C_7–C_{40}$-arylalkyl, $C_7–C_{40}$-alkylaryl or $C_8–C_{40}$-arylalkenyl,
or $R^2$ are identical or different and are each $C_1–C_{25}$-alkyl, $C_2–C_{25}$-alkenyl, $C_3–C_{15}$-alkylalkenyl, $C_6–C_{24}$-aryl, $C_5–C_{24}$-heteroaryl which together with the cyclopentadienyl ring form azapentalenes, thiapentalenes of phosphapentalenes, $C_7–C_{30}$-arylalkyl, $C_7–C_{30}$-alkylaryl, fluorinated $C_1–C_{25}$-alkyl, fluorinated $C_6–C_{24}$-aryl, fluorinated $C_7–C_{30}$-arylalkyl, fluorinated $C_7–C_{30}$-alkylaryl or $C_1–C_{12}$-alkoxy,
or two or more radicals $R^2$ are joined to one another so that the radicals $R^2$ and the atoms of the cyclopentadienyl ring which connect them form a $C_4–C_{24}$ ring system which is optionally substituted,
$R^5$ and $R^6$ are identical or different and are each a hydrogen atom or $Si(R^{12})_3$, where $R^{12}$ are identical or different and are each a hydrogen atom, $C_1–C_{20}$-alkyl, $C_1–C_{10}$-fluoroalkyl, $C_1–C_{10}$-alkoxy, $C_6–C_{20}$-aryl, $C_6–C_{10}$-fluoroaryl, $C_6–C_{10}$-aryloxy, $C_2–C_{10}$-alkenyl, $C_7–C_{40}$-arylalkyl, $C_7–C_{40}$-alkylaryl or $C_8–C_{40}$-arylalkenyl,
or $R^5$ and $R^6$ are identical or different and are each $C_1–C_{25}$-alkyl, $C_2–C_{25}$-alkenyl, $C_3–C_{15}$-alkylalkenyl, $C_6–C_{24}$-aryl, $C_5–C_{24}$-heteroaryl, $C_7–C_{30}$-arylalkyl, $C_7–C_{30}$-alkylaryl, fluorinated $C_1–C_{25}$-alkyl, fluorinated $C_6–C_{24}$-aryl, fluorinated $C_7–C_{30}$-arylalkyl, fluorinated $C_7–C_{30}$-alkylaryl or $C_1–C_{12}$-alkoxy,
or the radicals $R^5$ and $R^6$ are joined to one another so that the radicals $R^5$ and $R^6$ form a $C_4–C_{24}$-ring system which is optionally substituted,
$R^{60}$ is hydrogen,
L are identical or different and are each a hydrogen atom, $C_1–C_{10}$-alkyl or $C_6–C_{10}$-aryl, a halogen atom or $OR^9$, $SR^9$, $OSiR^9_3$, $SiR^9_3$, $PR^9_2$ or $NR^9_2$, wherein $R^9$ is a halogen atom, a $C_1–C_{10}$-alkyl group, a halogenated $C_1–C_{10}$-alkyl group, a $C_6–C_{20}$-aryl group or a halogenated $C_2–C_{20}$-aryl group, or L is a toluenesulfonyl, trifluoroacetyl, trifluoroacetoxyl, trifluoromethanesulfonyl, nonafluorobutanesulfonyl or 2,2,2-trifluoroethanesulfonyl group,
n is 2.

4. The compound as claimed in claim 1, wherein Z is $M^2R^{10}R^{11}$, wherein $M^2$ is carbon, silicon, germanium, boron or tin and $R^{10}$ and $R^{11}$ are identical or different and are each a $C_1–C_{20}$-hydrocarbon-containing group.

5. The compound as claimed in claim 4, wherein Z is $CH_2$, $CH_2CH_2$, $CH(CH_3)CH_2$, $CH(C_4H_9)C(CH_3)_2$, $C(CH_3)_2$, $C(CH_3)_2Si$, $(CH_3)_2Ge$, $(CH_3)_2Sn$, $(C_6H_5)_2Si$, $(C_6H_5)(CH_3)$ Si, $(C_6H_5)_2Ge$, $(CH_3)_3Si$—$Si(CH_3(C_6H_5)_2$—Sn, $(CH_2)_4Si$, $CH_2Si(CH_3)_2$, o-$C_6H_4$ or 2,2'-$(C_6H_4)_2$ or a 1,2-(1-methylethanediyl), 1,2-(1,1-dimethylethanediyl) or 1,2-(1, 2-dimethylethanediyl) bridge.

6. The compound as claimed in claim 1, wherein the formula (I) represents a bridged organometallic compound in which v is 1 and the cyclopentadienyl ring is substituted by $R^2$ so as to form an indenyl ring.

7. A compound of the formula (II):

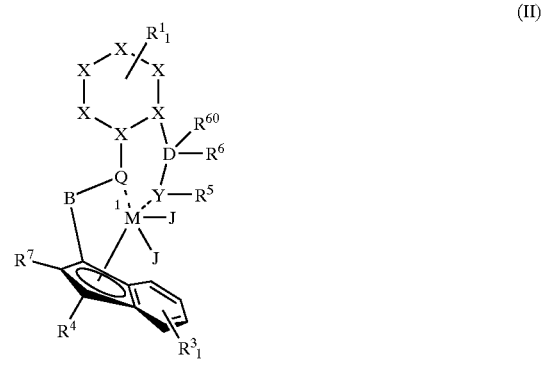

(II)

wherein $M^1$ is Ti, Zr or Hf, $R^1$ are identical or different and are each a hydrogen atom, $O\text{—}Si(R^{12})_3$ or $Si(R^{12})_3$, wherein $R^{12}$ are identical or different and are each a hydrogen atom or a $C_1\text{–}C_{40}$ group which is optionally fluorinated, or $R^1$ identical or different and are each a $C_1\text{–}C_{30}$ group which is optionally fluorinated, or two or more radicals $R^1$ are joined to one another so that the radicals $R^1$ and the atoms connecting them form a $C_4\text{–}C_{24}$ ring system which is optionally substituted, $R^4$ and $R^7$ independently are each a hydrogen atom, a $C_1\text{–}C_{20}$ group which is optionally fluorinated, $R^5$ and $R^6$ are identical or different and are each a hydrogen atom or $Si(R^{12})_3$, wherein $R^{12}$ are identical or different and are each a hydrogen atom or a $C_1\text{–}C_{40}$ group which is optionally fluorinated, or the radicals $R^5$ and $R^6$ are joined to one another so that the radicals $R^5$ and $R^6$ form a $C_4\text{–}C_{24}$ ring system which is optionally substituted, $R^3$ is a hydrogen atom, a halogen atom or a $C_1\text{–}C_{20}$ group, which is optionally fluorinated, or two or more radicals $R^3$ form a monocyclic or polycyclic ring system which is optionally substituted, $R^{60}$ is a hydrogen atom or a $C_1\text{–}C_{12}$-alkyl group, J is a halogen atom, an alkyl group or a substituted or unsubstituted phenoxide, Q, Y and D independently are each an element of main group III, IV, V or VI of the Periodic Table of the Elements, X are identical or different and are each an element of main group III, IV, V or VI of the Periodic Table of the Elements, wherein the radicals X together form a cyclic system in which one or more carbon atoms is optionally replaced by N, O, S or B, and said cyclic system is optionally substituted by $R^1$, l and i are identical or different and are each an integer from 0 to 4, B is a bridging structural element, $R^{60}$ is a hydrogen atom.

8. The compound as claimed in claim 7, wherein $M^1$ is zirconium, $R^1$ are identical or different are each a hydrogen atom, $O\text{—}Si(R^{12})_3$ or $Si(R^{12})_3$ wherein $R^{12}$ are identical or different and each are a hydrogen atom, $C_1\text{–}C_{20}$-alkyl, $C_1\text{–}C_{10}$-fluoroalkyl, $C_1\text{–}C_{10}$-alkoxy, $C_6\text{–}C_{20}$-aryl, $C_6\text{–}C_{10}$-fluoroaryl, $C_6\text{–}C_{10}$-aryloxy, $C_2\text{–}C_{10}$-alkenyl, $C_7\text{–}C_{40}$-arylalkyl, $C_7\text{–}C_{40}$-alkylaryl or $C_8C_{40}$-arylalkenyl or $R^1$ are identical or different and each are a $C_1\text{–}C_{25}$-alkyl, $C_2\text{–}C_{25}$-alkenyl, $C_3\text{–}C_{15}$-alkylalkenyl, $C_6\text{–}C_{24}$-aryl, $C_5\text{–}C_{24}$-heteroaryl, $C_7\text{–}C_{30}$-arylalkyl, $C_7\text{–}C_{30}$-alkylaryl, fluorinated $C_1\text{–}C_{25}$-alkyl, fluorinated $C_6\text{–}C_{24}$-aryl, fluorinated $C_7\text{–}C_{30}$-arylalkyl fluorinated $C_7\text{–}C_{30}$-alkylaryl or $C_1\text{–}C_{12}$-alkoxy, or two or more radicals $R^1$ are joined to one another so that the radicals $R^1$ and the atoms connecting them form a $C_4\text{–}C_{24}$ ring system which is optionally substituted, $R^4$ and $R^7$ independently are each a hydrogen atom, a $C_1\text{–}C_{18}$-alkyl, $C_2\text{–}C_{10}$-alkenyl, $C_3\text{–}C_{15}$-alkylalkenyl, $C_6\text{–}C_{18}$-aryl, $C_5\text{–}C_{18}$-heteroaryl, $C_7\text{–}C_{20}$-arylalkyl, $C_7\text{–}C_{20}$-alkylaryl, fluorinated $C_1\text{–}C_{12}$-alkyl, fluorinated $C_6\text{–}C_{18}$-aryl, fluorinated $C_7\text{–}C_{20}$-arylalkyl or fluorinated $C_7\text{–}C_{20}$-alkylaryl, $R^5$ and $R^6$ are identical or different and each are a hydrogen atom, $Si(R^{12})_3$ or $R^{12}(_3)$ wherein $R^{12}$ is as defined above or $R^5$ and $R^6$ are identical or different and each are a $C_1\text{–}C_{25}$-alkyl, $C_2\text{–}C_{25}$-alkenyl, $C_3\text{–}C_{15}$-alkylalkenyl, $C_6\text{–}C_{24}$-aryl, $C_5\text{–}C_{24}$-heteroaryl, $C_7\text{–}C_{30}$-arylalkenyl, $C_7\text{–}C_{30}$-alkylaryl, fluorinated $C_1\text{–}C_{25}$-alkyl, fluorinated $C_6\text{–}C_{24}$-aryl, fluorinated $C_7\text{–}C_{30}$-arylalkyl, fluorinated $C_7\text{–}C_{30}$-alkylaryl or $C_1\text{–}C_{12}$-alkoxy or the radicals $R^5$ and $R^6$ are joined to one another so that the radicals $R^5$ and $R^6$ form a $C_4\text{–}C_{24}$ ring system which is optionally substituted, $R^3$ is a hydrogen atom, a halogen atom, a linear $C_1\text{–}C_{18}$-alkyl group, a branch $C_1\text{–}C_{18}$-alkyl group, a $C_2\text{–}C_{10}$-alkenyl, $C_3\text{–}C_{15}$-alkylalkenyl, $C_6\text{–}C_{18}$ group which is optionally substituted, a $C_5\text{–}C_{18}$-heteroaryl, $C_7\text{–}C_{20}$-arylalkyl, $C_7\text{–}C_{20}$-alkylaryl, fluorinated $C_1\text{–}C_{12}$-alkyl, fluorinated $C_6\text{–}C_{18}$-aryl, fluorinated $C_7\text{–}C_{20}$-arylalkyl or fluorinated $C_7\text{–}C_{20}$-alkylaryl, or two or more radicals $R^3$ form a monocyclic or polycyclic ring system which is optionally substituted, $R^{60}$ is a hydrogen atom, J is a chlorine, $C_1\text{–}C_{18}$-alkyl or a substituted or unsubstituted phenoxide, Q, Y and D independently are each boron, carbon, silicon, nitrogen, oxygen or sulfur, X are identical or different and each are boron, carbon, silicon, nitrogen, oxygen or sulfur or in the radicals X together form an aromatic system or a cyclic aliphatic system in which one or more of the carbon atoms is replaced by N, O, S or B and said aromatic or said cyclic aliphatic system is optionally substituted by $R^1$ and l and i are identical or different and are each an integer 1 or 2.

9. The compound as claimed in claim 8, wherein $R^4$ and $R^7$ are identical or different and are each a hydrogen atom, a methyl, ethyl, n-butyl, n-hexyl, cyclohexyl, octyl, $C_2\text{–}C_{10}$-alkenyl, $C_3\text{–}C_{15}$-alkylalkenyl, $C_6\text{–}C_{18}$-aryl, $C_5\text{–}C_{18}$-heteroaryl, $C_7\text{–}C_{20}$-arylalkyl, $C_7\text{–}C_{20}$-alkylaryl, fluorinated $C_1\text{–}C_{12}$-alkyl, fluorinated $C_6\text{–}C_{18}$-aryl, fluorinated $C_7\text{–}C_{20}$-arylalkyl or fluorinated $C_7\text{–}C_{20}$-alkylaryl, $R^5$ and $R^6$ are identical or different and each are a hydrogen atom or $Si(R^{12})_3$ or methyl, ethyl, tert-butyl, n-hexyl, cyclohexyl, octyl $C_2\text{–}C_{25}$-alkenyl, $C_2\text{–}C_{25}$-alkenyl, $C_3\text{–}C_{15}$-alkylalkenyl, $C_6\text{–}C_{24}$-aryl, $C_5\text{–}C_{24}$-heteroaryl, $C_7\text{–}C_{30}$-arylalkyl, $C_7\text{–}C_{30}$-alkylaryl, fluorinated $C_1\text{–}C_{25}$-alkyl, fluorinated $C_6\text{–}C_{24}$-aryl, fluorinated $C_7\text{–}C_{30}$-arylalkyl fluorinated $C_7\text{–}C_{30}$-alkylaryl or $C_1\text{–}C_{12}$-alkoxy, or the radicals $R^5$ and $R^6$ may be joined to one another so that the radicals $R^5$ and $R^6$ form a $C_4\text{–}C_{24}$ ring system which is optionally substituted, $R^3$ is a hydrogen atom, halogen atom, methyl, methyl, ethyl, tert-butyl, cyclohexyl, octyl, $C_2\text{–}C_{10}$-alkenyl, $C_3\text{–}C_{15}$-alkylalkenyl, phenyl, tolyl, xylyl, tert-butylphenyl, ethylphenyl, naphthyl, acenaphthyl, phenylethenyl, anthracenyl, $C_5\text{–}C_{18}$-heteroaryl, $C_7\text{–}C_{20}$-arylalkyl, $C_7\text{–}C_{20}$-alkylaryl, fluorinated $C_1\text{–}C_{12}$-alkyl, fluorinated $C_6\text{–}C_{18}$-aryl, fluorinated $C_7\text{–}C_{20}$-arylalkyl or fluorinated $C_7\text{–}C_{20}$-alkylaryl, or two or more radicals $R^3$ forms a monocyclic or polycyclic ring system which is optionally substituted, J is chlorine, methyl, ethyl, tert-butyl or a substituted or unsubstituted phenoxide, X is boron, carbon, silicon, nitrogen, oxygen or sulfur or wherein the radicals X together form phenyl, naphthyl, adamantyl, fluorenyl,cyclohexyl, boratabenzine which is optionally substituted by $R^1$, l and I are 1.

10. The compound as claimed in claim 8, wherein the indenyl ring is substituted in the 2 position, the 4 position, the 2,4,5 positions, the 2,4,6 positions, the 2,4,7 positions or the 2,4,5,6 positions by one or more radicals $R^3$ which are each a $C_1$–$C_{20}$ group, or where two or more substituents $R^3$ also together form a ring system.

11. The compound as claimed in claim 8, wherein the indenyl ring is substituted in the 2 position, the 4 position, the 2,4,5 positions, the 2,4,6 positions, the 2,4,7 positions or the 2,4,5,6 positions by one or more radicals $R^3$ which are each a $C_1$–$C_{18}$-alkyl or $C_6$–$C_{18}$-aryl or where two or more substituents $R^3$ also together form a ring system.

12. A compound as claimed in claim 9, wherein $M^1$ is zirconium, $R^7$ is a hydrogen atom or a linear or branched $C_1$–$C_{12}$-alkyl group, $R^5$ is a hydrogen atom, a halogen atom or a linear or branched $C_1$–$C_8$-alkyl group, $C_2$–$C_6$-alkenyl, $C_3$–$C_6$-alkylalkenyl, a $C_6$–$C_{18}$-aryl group which is optionally substituted, $C_5$–$C_{18}$-heteroaryl, $C_7$–$C_{12}$-arylalkyl, $C_7$–$C_{12}$-alkylaryl, fluorinated $C_1$–$C_8$-alkyl, fluorinated $C_6$–$C_{18}$-aryl, fluorinated $C_7$–$C_{12}$-arylalkyl or fluorinated $C_7$–$C_{12}$-alkylaryl, $R^6$ are identical or different and are each a hydrogen atom or a $C_1$–$C_{12}$-alkyl group, $R^3$ is a hydrogen atom, a halogen atom or a linear or branched $C_1$–$C_8$-alkyl group, $C_2$–$C_6$-alkenyl, $C_3$–$C_6$-alkylalkenyl, a $C_6$–$C_{18}$-aryl group, a substituted $C_6$–$C_{18}$-aryl group, $C_5$–$C_{18}$-heteroaryl, $C_7$–$C_{12}$-arylalkyl, $C_7$–$C_{12}$-alkylaryl, fluorinated $C_1$–$C_8$-alkyl, fluorinated $C_6$–$C_{18}$-aryl, fluorinated $C_7$–$C_{12}$-arylalkyl or fluorinated $C_7$–$C_{12}$-alkylaryl, J is chlorine or methyl, Q, Y and D are each, independently of one another, an element of main group IV, V or VI of the Periodic Table of the Elements, X may be identical or different and are each an element of main group IV, V or VI of the Periodic Table of the Elements, I and i are identical or different and are each an integer from 0 to 4, B is a bridging structural element and is a divalent radical $Si(Me)_2$, $Si(Ph)_2$, $Si(E_2)$, $Si(MePh)$, $CH_2$, $CH_2CH_2$, $(CH_3)_3Si—Si(CH_3)$ where Me is methyl, Et is ethyl and Ph is phenyl.

13. The compound as claimed in claim 7, wherein B is an $M^3R^{13}R^{14}$ group, wherein $M^3$ is silicon or carbon and $R^{13}$ and $R^4$ are identical or different and are each $C_1$–$C_{10}$-alkyl, $C_6$–$C_{14}$-aryl or trimethylsilyl.

14. A compound of the formula (IIa):

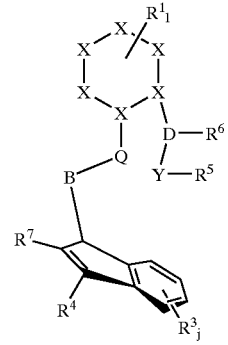

(IIa)

wherein $R^1$ are identical or different and are each a hydrogen atom, $O$—$Si(R^{12})_3$ or $Si(R^{12})_3$, wherein $R^{12}$ are identical or different and are each a hydrogen atom or a $C_1$–$C_{40}$ group which is optionally fluorinated, or $R^1$ are identical or different and are each a $C_1$–$C_{30}$ group which is optionally fluorinated, or two or more radicals $R^1$ are joined to one another so that the radicals $R^1$ and the atoms connecting them form a $C_4$–$C_{24}$ ring system which is optionally substituted, $R^4$ and $R^7$ independently are each a hydrogen atom, a $C_1$–$C_{20}$ group which is optionally fluorinated, $R^5$ and $R^6$ independently are identical or different and are each a hydrogen atom or $Si(R^{12})_3$, wherein $R^{12}$ is defined above, or $R^5$ and $R^6$ are identical or different and are each a $C_1$–$C_{30}$ group which is optionally fluorinated, or the radicals $R^5$ and $R^6$ are joined to one another so that the radicals $R^5$ and $R^6$ form a $C_4$–$C_{24}$ ring system which is optionally substituted, $R^3$ is a hydrogen atom, a halogen atom or a $C_1$–$C_{20}$ group which is optionally fluorinated, or two or more radicals $R^3$ form a monocyclic or polycyclic ring system which is optionally substituted, Q, Y and D independently are each an element of main group III, IV, V or VI of the Periodic Table of the Elements, X are identical or different and are each an element of main group III, IV, V or VI of the Periodic Table of the Elements, or wherein the radicals X together form cyclic systems in which one or more carbon atoms is optionally replaced by N, O, S or B, which is optionally substituted by $R^1$, 1 and i are identical or different and are each an integer from 0 to 4, B is a bridging structural element.

15. The compound as claimed in claim 14, wherein $R^1$ are identical or different and are each a hydrogen atom, $O$—$Si(R^{12})_3$ or $Si(R^{12})_3$ wherein $R^{12}$ are identical or different are each a hydrogen atom, $C_1$–$C_{20}$-alkyl, $C_1$–$C_{10}$-fluoroalkyl, $C_1$–$C_{10}$-alkoxy, $C_6$–$C_{20}$-axyl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl or $R^1$ are identical or different and each are a $C_1$–$C_{25}$-alkyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl $C_7$–$C_{30}$- alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^1$ are joined to one another so that the radicals $R^1$ and the atoms connecting them form a $C_4$–$C_{24}$ ring system which is optionally substituted, $R^4$ and $R^7$ independently are each a hydrogen atom, $C_1$–$C_{18}$-alkyl $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, $R^5$ and $R^6$ are identical or different and each are a hydrogen atom or $Si(R^{12})_3$ wherein $R^{12}$ is defined above or $R^5$ and $R^6$ are identical or different and each are a $C_1$–$C_{25}$-alkyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or the radicals $R^5$ and $R^6$ are joined to one another so that the radicals $R^5$ and $R^6$ form a $C_4$–$C_{24}$ ring system which is optionally substituted, $R^3$ is a hydrogen atom, halogen atom, a linear $C_1$–$C_{18}$-alkyl, a branch $C_1$–$C_{18}$-alkyl, $C_2$–$C_{10}$-alkenyl, $C_3$–$C_{15}$-alkylalkenyl, a $C_6$–$C_{18}$-aryl group which is optionally substituted, a $C_5$–$C_{18}$-heteroaryl, a $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or a fluorinated $C_7$–$C_{20}$-alkylaryl or two or more radicals $R^3$ to form a monocyclic or polycyclic ring system which is optionally substituted, Q, Y and D independently are boron, carbon, silicon, nitrogen, oxygen or sulfur, X are identical or different and each are boron, carbon, silicon, nitrogen, oxygen or sulfur or wherein the radicals X together form an aromatic or cyclic aliphatic cyclic system in which one or more carbon atoms is optionally replaced by N, O, S or B and said aromatic or aliphatic cyclic system is optionally further substituted by $R^1$.

16. The compound as claimed in claim 15, wherein $R^4$ and $R^7$ are independently or each hydrogen atom, methyl, ethyl, n-butyl, n-hexyl, cyclohexyl, octyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, $R^5$ and $R^6$ are identical or different and each are a hydrogen atom, $Si(R^{12})_3$, methyl, ethyl, tert-butyl, n-hexyl, cyclohexyl, octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or the radicals $R^5$ and $R^6$ are joined to one another so that the radicals $R^5$ and $R^6$ form a $C_4$–$C_{24}$ ring system which is optionally substituted, $R^3$ is a hydrogen atom, a halogen atom, methyl, ethyl, tert-butyl, cyclohexyl, octyl, $C_2$–$C_{10}$-alkenyl, $C_3$–$C_{15}$-alkylalkenyl, phenyl, tolyl, xylyl, tert-butylphenyl, ethylphenyl, naphthyl, acenaphthyl, phenylethenyl or anthracenyl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, or two or more radicals $R^3$ form a monocyclic or polycyclic ring system which is optionally substituted, and X is identical or different and each are boron, carbon, silicon, nitrogen, oxygen or sulfur or wherein the X radicals together form phenyl, naphthyl, adamantyl, fluorenyl, cyclohexyl or boratabenzine which in turn is optionally substituted by $R^1$.

17. A catalyst system comprising one or more compounds as claimed in claim 1, and one or more cocatalysts.

18. The catalyst system as claimed in claim 17 which further comprises one or more supports.

19. A process to prepare the compound as claimed in claim 7 which comprises reacting the compound of the formula IIa

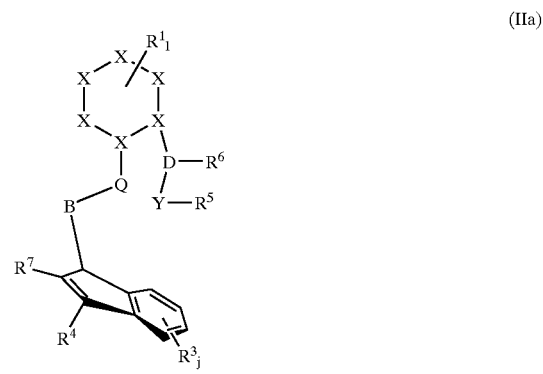

(IIa)

20. The process for preparing a polyolefin which comprises polymerization of one or more olefins in the presence of one or more compounds as claimed in claim 1, wherein $R^1, R^4, R^5, R^6, R^7, R^3, I, L, X, D$ and $Y$ and $Q$ are defined in claim 22 with $M^1J_2$ wherein $M^1$ is Ti Zr or Hf and J is a halogen atom, an alkyl group or a substituted or unsubstituted phenoxide.

* * * * *